(12) United States Patent
Wei

(10) Patent No.: US 10,881,796 B2
(45) Date of Patent: Jan. 5, 2021

(54) AUTOMATIC MEDICATION INJECTION DEVICE

(71) Applicant: Min Wei, Carmel, IN (US)

(72) Inventor: Min Wei, Carmel, IN (US)

(73) Assignee: Min Wei, Carmel, IN (US)

(*) Notice: Subject to any disclaimer, the term of this patent is extended or adjusted under 35 U.S.C. 154(b) by 587 days.

(21) Appl. No.: 15/109,478

(22) PCT Filed: Mar. 7, 2015

(86) PCT No.: PCT/US2015/019326
§ 371 (c)(1),
(2) Date: Jul. 1, 2016

(87) PCT Pub. No.: WO2015/138261
PCT Pub. Date: Sep. 17, 2015

(65) Prior Publication Data
US 2016/0331900 A1    Nov. 17, 2016

Related U.S. Application Data

(60) Provisional application No. 61/951,590, filed on Mar. 12, 2014.

(51) Int. Cl.
*A61M 5/20* (2006.01)
*A61M 5/32* (2006.01)
(Continued)

(52) U.S. Cl.
CPC .............. *A61M 5/2033* (2013.01); *A61J 1/16* (2013.01); *A61M 5/3204* (2013.01); *A61M 5/326* (2013.01); *B65D 1/36* (2013.01); *B65D 83/02* (2013.01); *A61M 5/008* (2013.01); *A61M 5/3129* (2013.01); *A61M 5/3134* (2013.01); *A61M 5/46* (2013.01); *A61M 2005/206* (2013.01); *A61M 2005/2013* (2013.01); *A61M 2005/2026* (2013.01); *A61M 2005/31518* (2013.01);
(Continued)

(58) Field of Classification Search
CPC .... A61M 5/31515; A61M 2005/31518; A61M 5/31511; A61M 5/2033
See application file for complete search history.

(56) References Cited

U.S. PATENT DOCUMENTS

| 5,295,965 A * | 3/1994 | Wilmot | A61M 5/2033 604/136 |
| 2013/0023822 A1* | 1/2013 | Edwards | A61M 5/2033 604/82 |
| 2015/0209505 A1* | 7/2015 | Hanson | A61M 5/1454 604/135 |

FOREIGN PATENT DOCUMENTS

WO   WO-2013119591 A1 *  8/2013   .......... A61M 5/2033

* cited by examiner

Primary Examiner — Matthew F Desanto
(74) Attorney, Agent, or Firm — Min Wei

(57) ABSTRACT

An automatic injection device is provided herein comprising a container body having a distal end and a proximal end; a piston locked at said proximal end of said container body before medication injection; a spring configured to bias said piston distally; a releasable restraining means configured to releasably restrain said piston in a locked state against said biasing of said spring, wherein, upon release of said releasable restraining means, said piston moves under force of said spring toward said distal end of said container body; an activation means configured to release said releasable means; a needle cap placed at said distal end of said container body; and a needle placed at said distal end of said container body.

15 Claims, 21 Drawing Sheets

(51) Int. Cl.
_B65D 1/36_     (2006.01)
_A61J 1/16_     (2006.01)
_B65D 83/02_    (2006.01)
_A61M 5/31_         (2006.01)
_A61M 5/46_         (2006.01)
_A61M 5/315_        (2006.01)
_B65B 3/00_         (2006.01)
_A61M 5/00_         (2006.01)

(52) U.S. Cl.
CPC ............... _A61M 2005/3258_ (2013.01); _A61M 2005/3267_ (2013.01); _B65B 3/003_ (2013.01)

FIG. 3
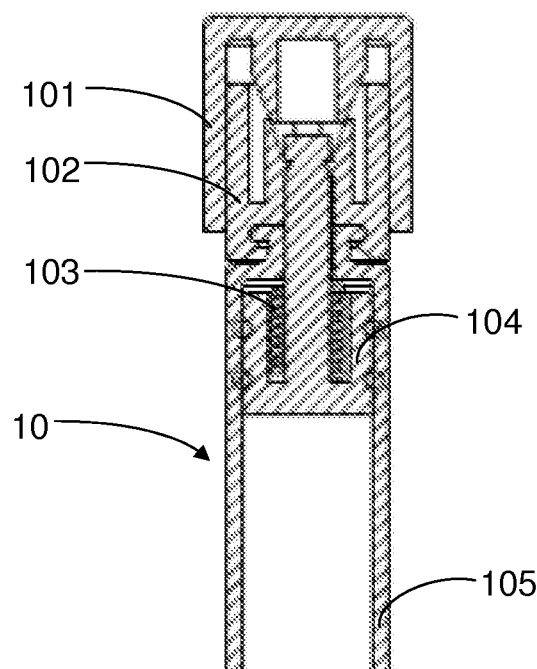
FIG. 3A
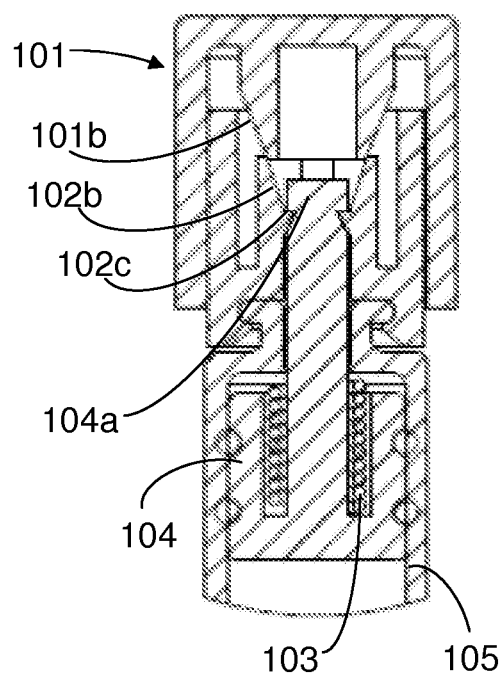
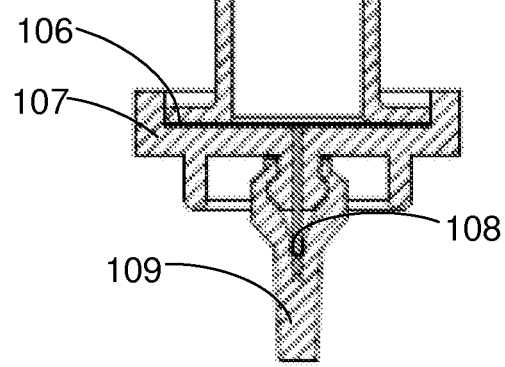
FIG. 3B
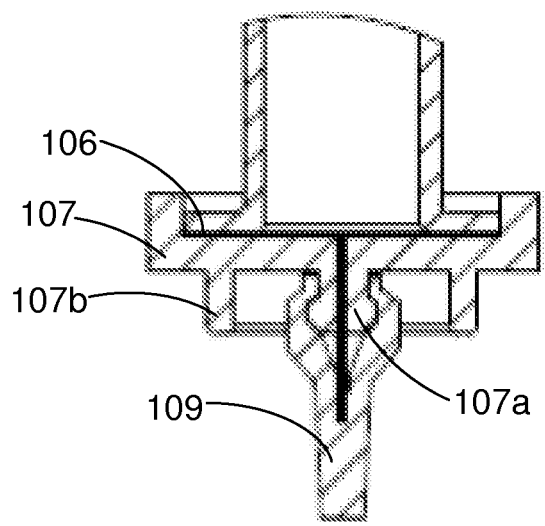

FIG. 6A
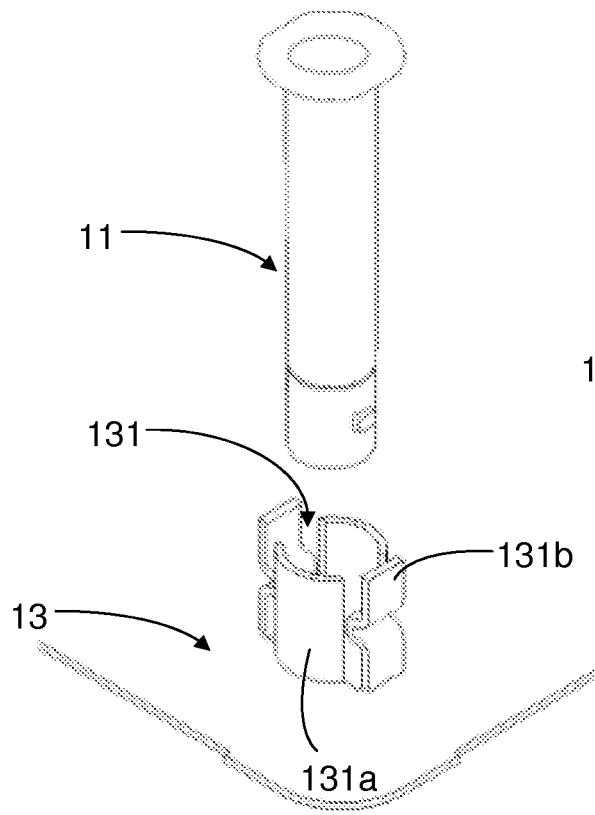
FIG. 6B
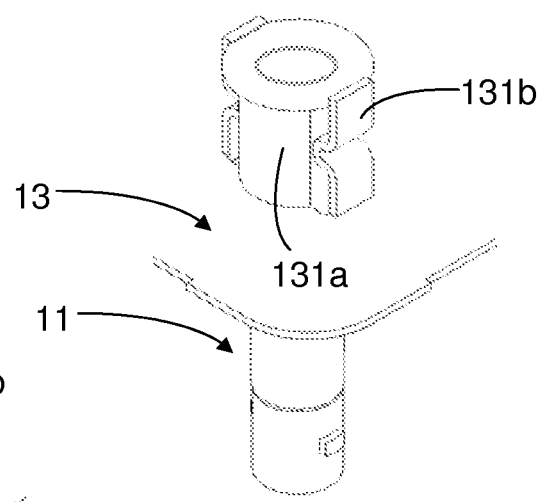
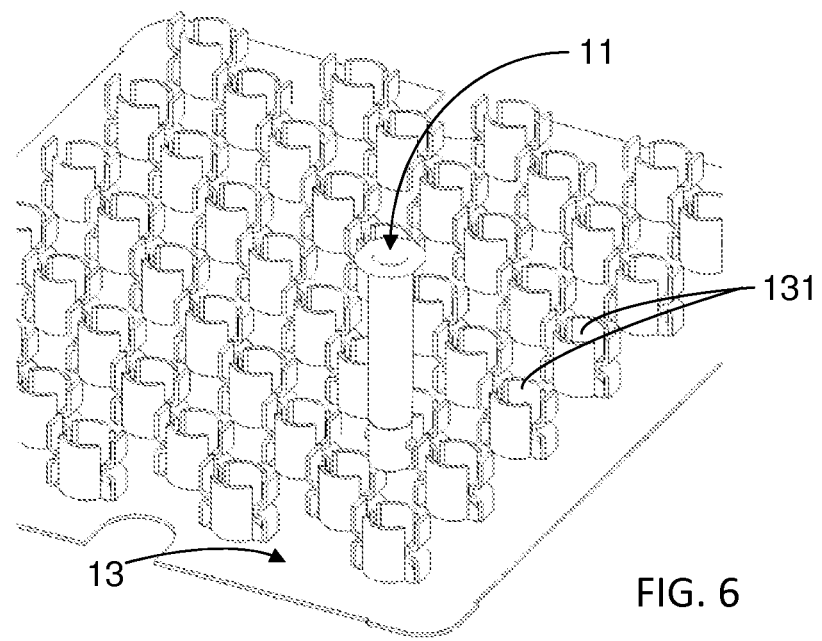
FIG. 6

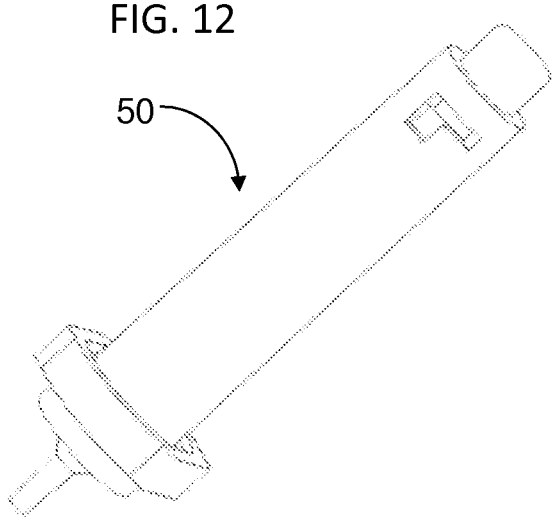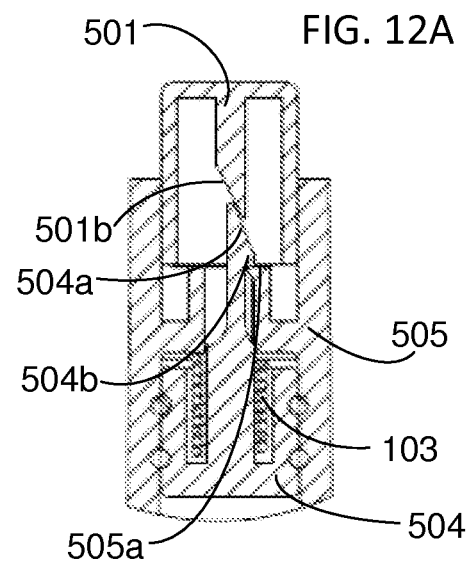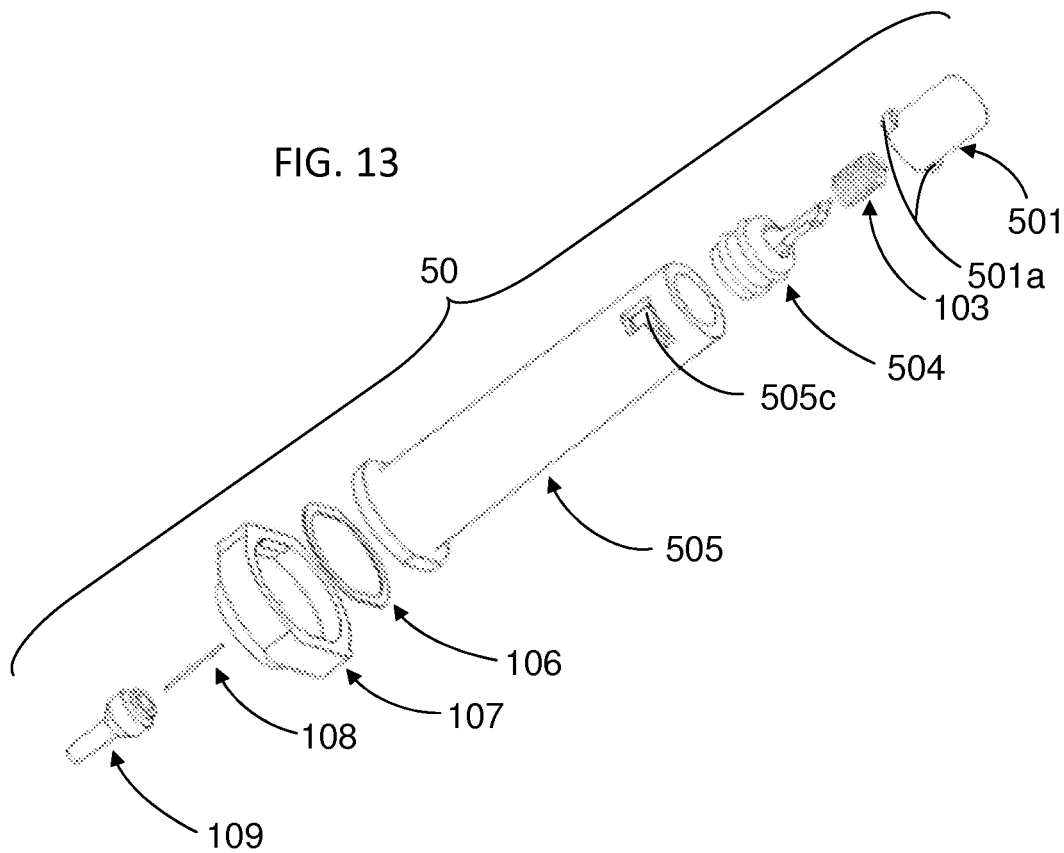

FIG. 14
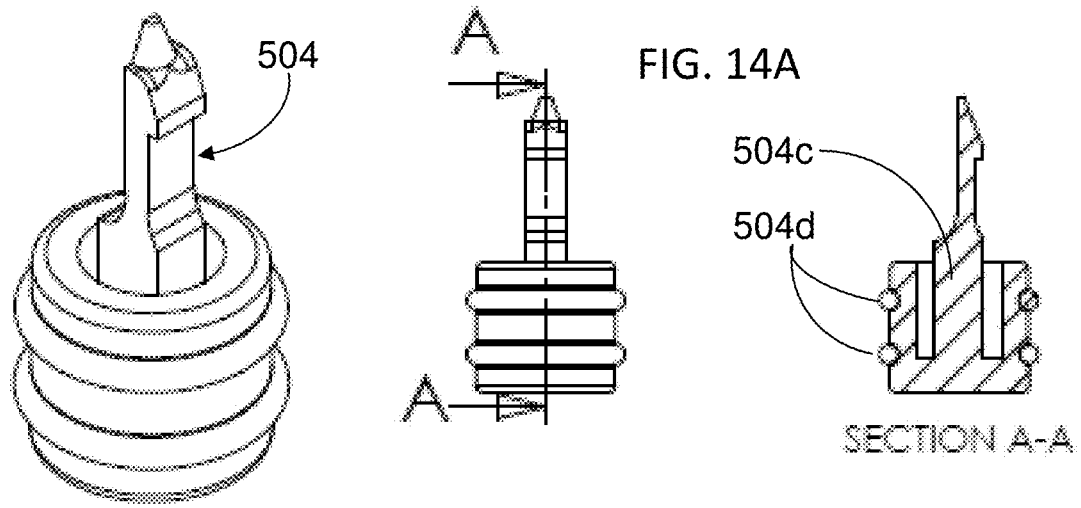
FIG. 14A
FIG. 15
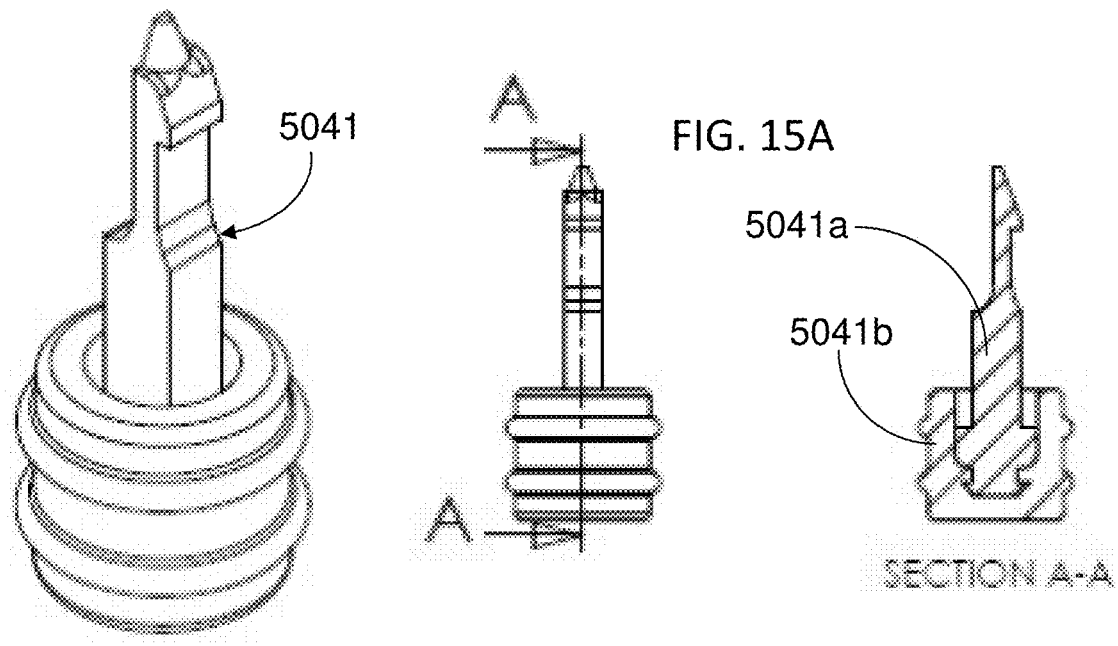
FIG. 15A

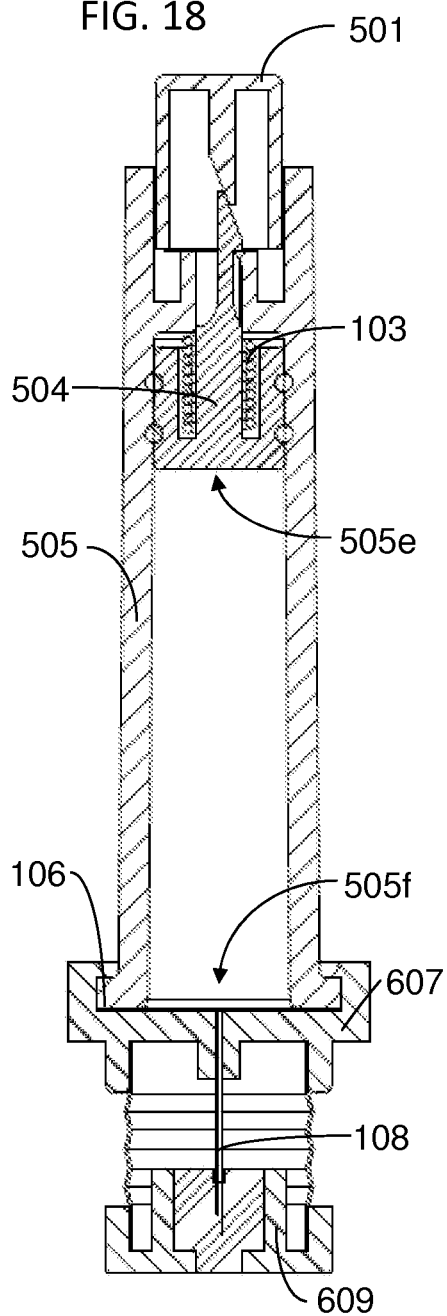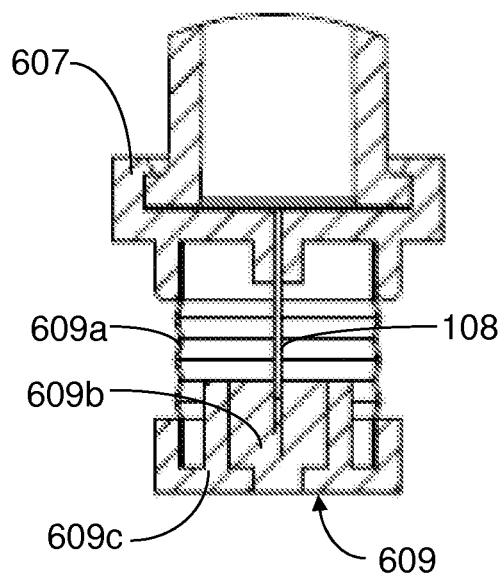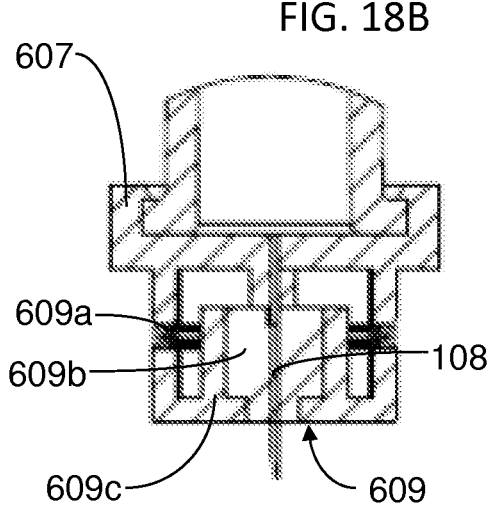

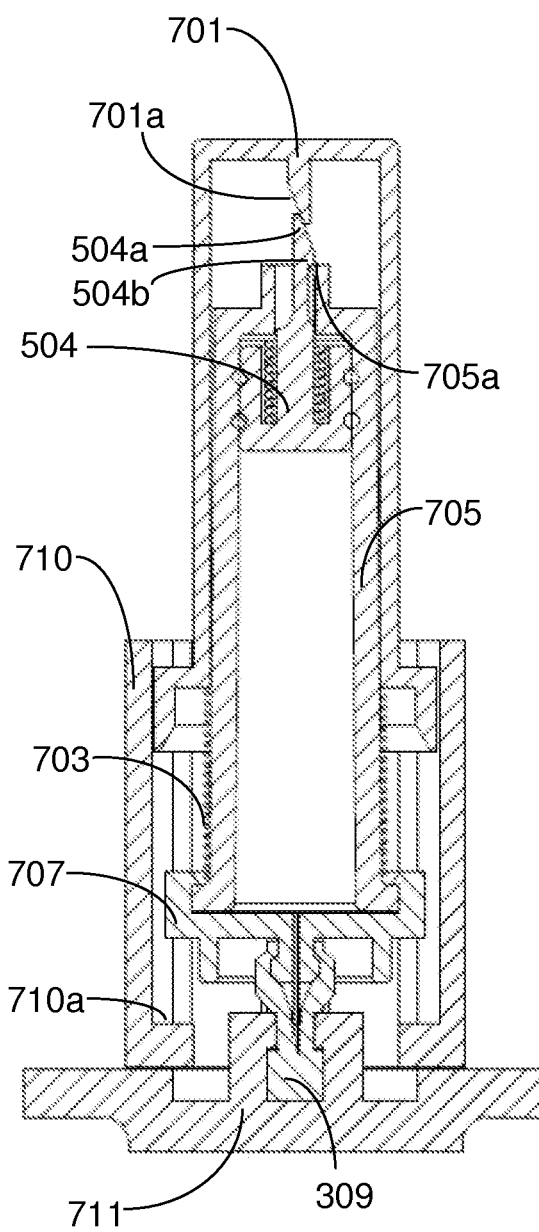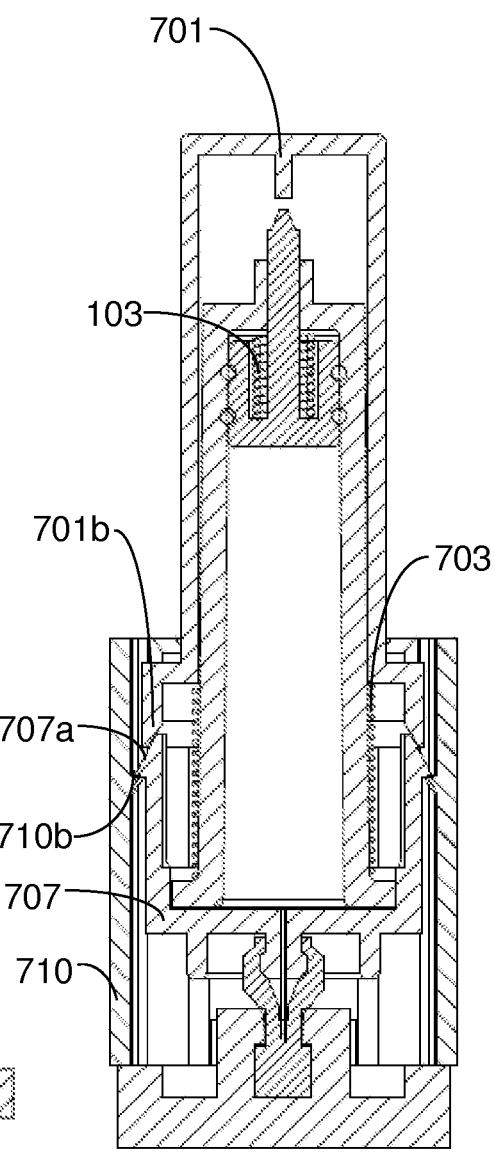

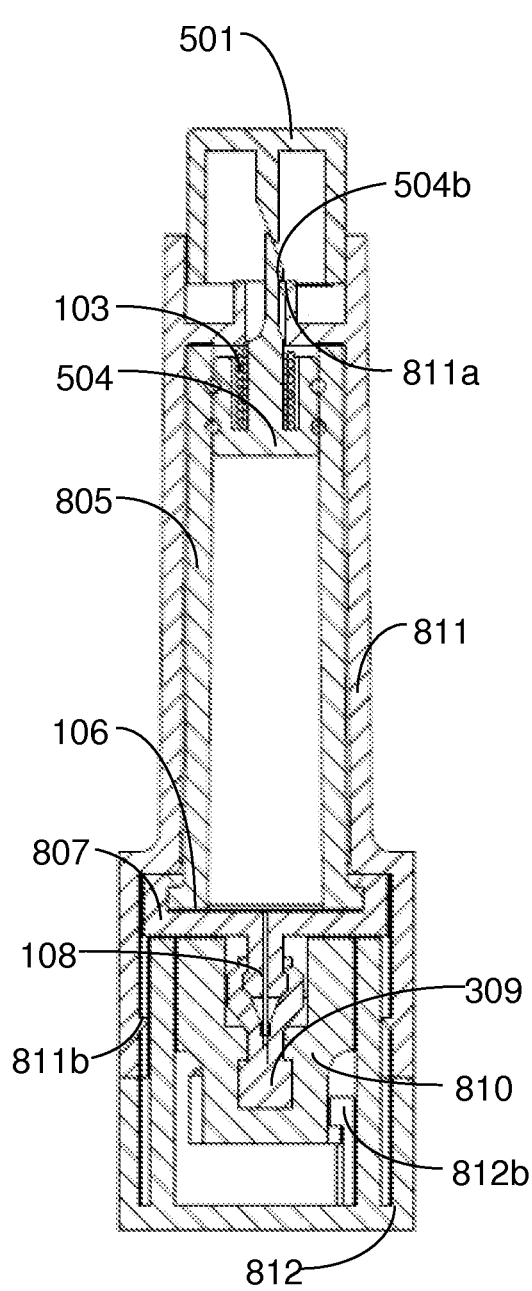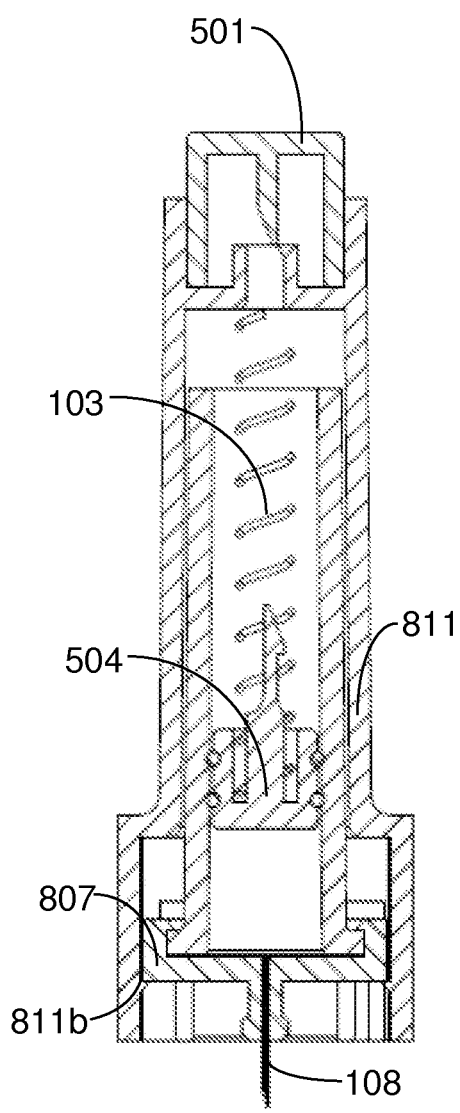

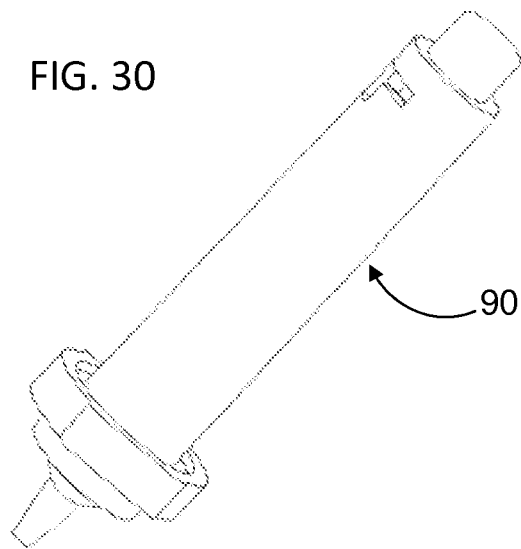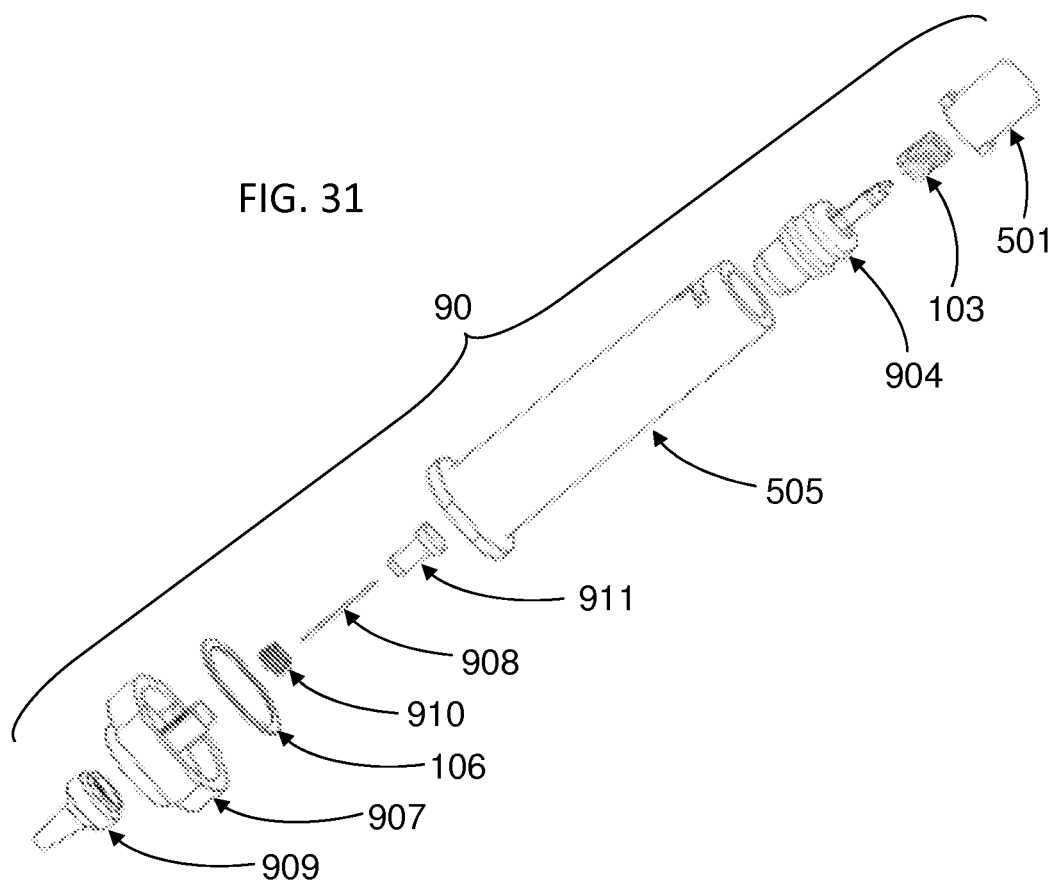

FIG. 32
FIG. 33
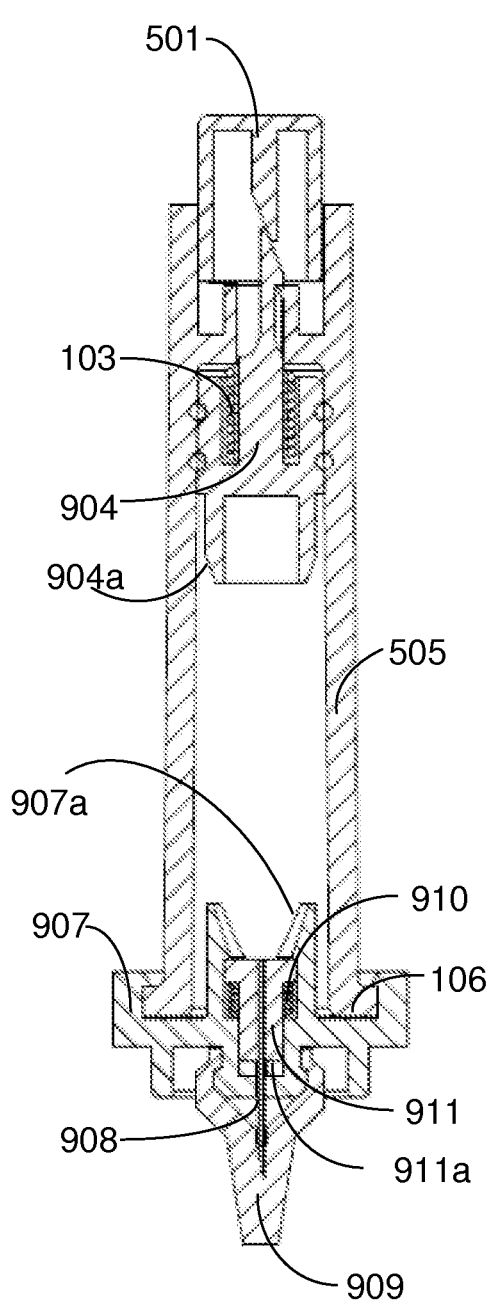
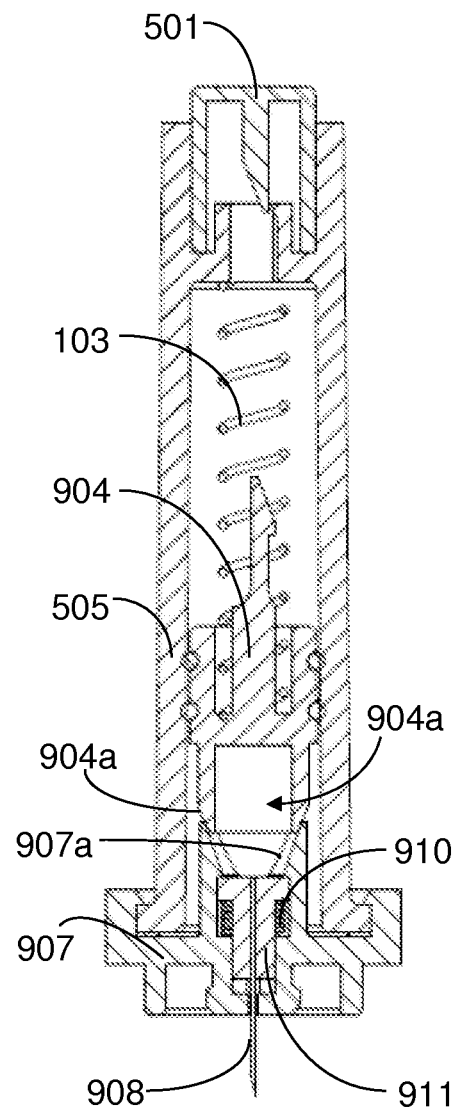

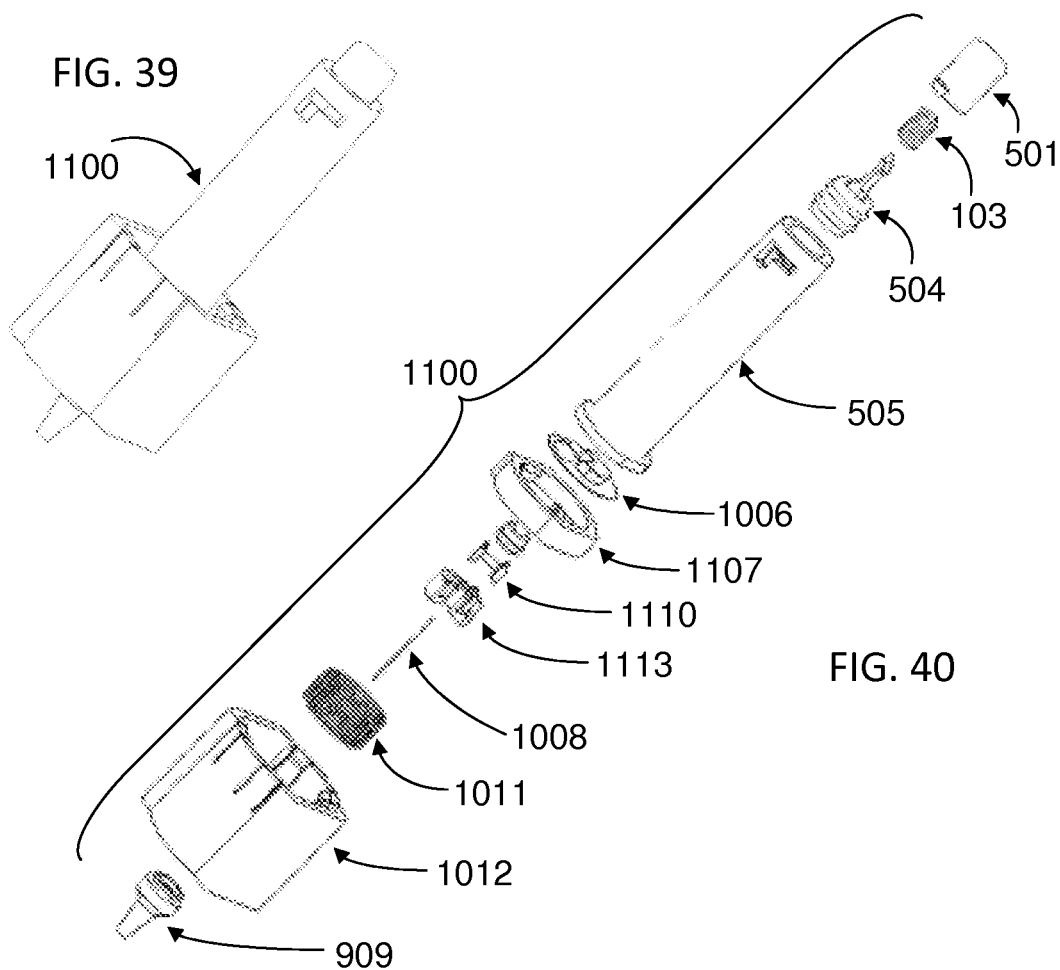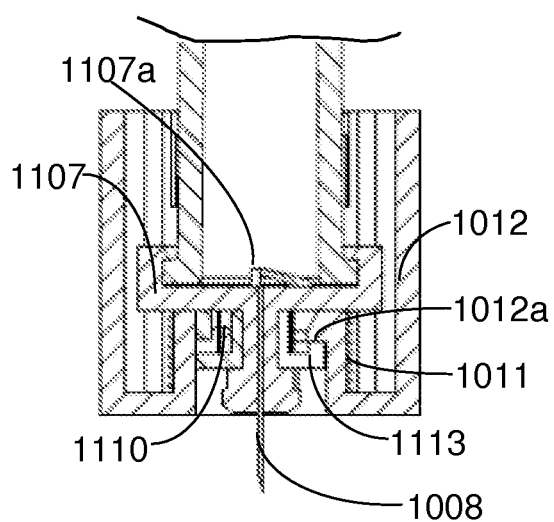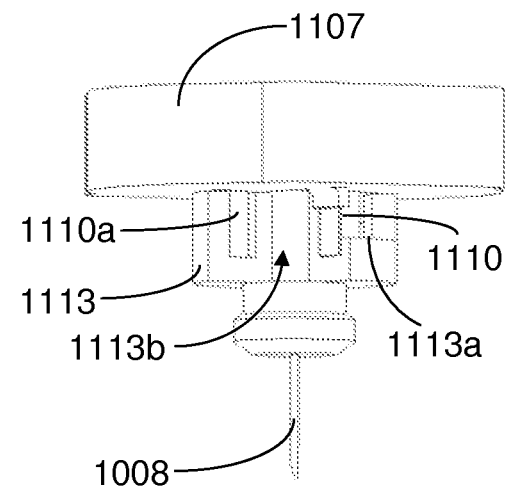

AUTOMATIC MEDICATION INJECTION DEVICE

TECHNICAL FIELD

The invention relates to an automatic injection device for delivering liquid medications.

BACKGROUND OF THE INVENTION

As the parenteral drugs become more and more popular, injection devices for liquid medications are expected to be widely used by patients and health care professionals. Prefilled syringe is a current form of medication injection device mainly used for liquid medications. Examples of prefilled syringe and the related manufacturing and packaging processes can be found in U.S. Pat. Nos. 6,189,292; 7,428,807; 7,431,157 and 8,196,741. The existing prefilled syringe is originally designed for manually drawing liquid medication from ampule or vial, and then delivering the medication solution through injection. This design lead to following challenges for automatic injection for liquid dosage form in prefilled format—
  a. The piston push rod is unnecessarily long and so cause the automatic injection device, for example, autoinjector, is unnecessarily large. This is especially true for pediatric patients.
  b. For prefilled syringe with staked needle, the most widely used prefilled syringe form, liquid medication filling and syringe piston, a seal component, placement happen at the same end of the syringe, which cause the unnecessary air bubble after the medication solution filling.
  c. The end-of-injection events, such like syringe retraction or needle protection cover extending-out, are controlled by relative position of piston push rod. This often causes pre-mature finish of the injection because of the part and assembly tolerance.
  d. The syringe piston is not at fixed at the initial position, and can move along the syringe barrel caused by change of air pressure, temperature or mechanical vibration. This movement can lead to loss of sterility seal.
  e. When plastic/polymer syringe is manufactured based on the current design, the syringe inner diameter at the needle end is often slightly smaller than the syringe inner diameter at the piston end because of injection molding manufacturing process limit. On the other hand, the piston driving spring used in auto-injector will have less mechanical force when it reaches to the needle end of the syringe. This design conflict forces the device designer to use unnecessary strong spring, which often cause the failure of the device component(s) during storage or injection operation.

Therefore, injection devices based on a novel design principal are in need.

SUMMARY OF THE INVENTION

It is an object of the present invention to provide an automatic injection device. This invention presents a series of the designs for the automatic injection device comprising: 1) a syringe-like container body; 2) a piston driven by a resilient spring that push the medication out of the container body during injection; 3) a needle assembly (device sub-assembly including a hollow needle) that is placed at the opposite end to the piston end of the container body. This invention is to overcome one or more of the disadvantages of the prior art.

It is an advantage of the present invention that the automatic injection device embodiments here have the piston locked at a fixed position in the syringe-like container body before use so that there is not risk of sterility breach.

It is an advantage of the present invention that the automatic injection device embodiments here do not have a long piston push rod. Therefore, the total length of the device is significantly smaller.

It is an advantage of the present invention that the medication filling into the device is from the needle end. Comparing to the medication filling from the piston end, the air bubble can be greatly reduced. Therefore, overall device size will be smaller. There will be less amount of air injected into patient. The injection dose accuracy will be higher. For drugs that are sensitive to oxygen, less amount of air space is also beneficial.

It is a further advantage that the syringe-like container body for the present invention can have a smaller inner cylindrical diameter at the piston end than the inner cylindrical diameter at the needle end. When the piston moves, inside of the container body, to the needle end, the friction force between the piston and the container body will become less due to the lesser amount of interference between the piston and the container body. As a result, unnecessary high compression force required for piston driving spring can be avoided. Moreover, the tapered construction of container body inner can make the injection molding process easier.

BRIEF DESCRIPTION OF THE DRAWINGS

The figures are schematic and simplied for clarity, and they just show details, which are essential to the understanding of the invention, while other details are left out. Throughout, the same reference numerals are used for identical or corresponding parts.

FIG. 3, FIG. 3A and FIG. 3B are cross-sectional views of the exemplary injection device assembly according to the invention.

FIG. 6, FIG. 6A and FIG. 6B show the packaging configuration for the container body sub-assembly of the exemplary injection device assembly according to the invention.

FIG. 9A is a cross-sectional view of the second alternative injection device assembly according to the invention.

FIG. 12 is a perspective view of the fourth alternative injection device assembly according to the invention.

FIG. 12A is a cross-sectional detailed view of the fourth alternative injection device assembly according to the invention.

FIG. 13 is an exploded view of the fourth alternative injection device assembly according to the invention.

FIG. 14, FIG. 14A and FIG. 15, FIG. 15A show two configurations of the piston according to the invention.

FIG. 18, FIG. 18A and FIG. 18B are cross-sectional views of the fifth alternative injection device assembly according to the invention.

FIG. 21 and FIG. 22 are cross-sectional views of the sixth alternative injection device assembly according to the invention.

FIG. 25 and FIG. 26 are cross-sectional views of the seventh alternative injection device assembly according to the invention.

FIG. 30 is a perspective view of the eighth alternative injection device assembly according to the invention.

FIG. 31 is an exploded view of the eighth alternative injection device assembly according to the invention.

FIG. 32 and FIG. 33 are cross-sectional views of the eighth alternative injection device assembly according to the invention.

FIG. 39 is a perspective view of the tenth alternative injection device assembly according to the invention.

FIG. 40 is an exploded view of the tenth alternative injection device assembly according to the invention.

FIG. 41 and FIG. 42 show the mechanism of the needle sub-assembly of the tenth alternative injection device assembly according to the invention.

Corresponding parts are marked with the same reference symbols in all figures.

DETAILED DESCRIPTION THE DRAWINGS

Figure 1:
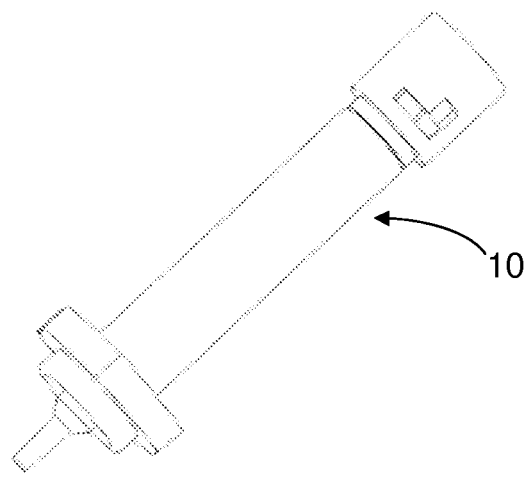
FIG. 1 is a perspective view of an exemplary injection device assembly according to the invention.
Figure 2:
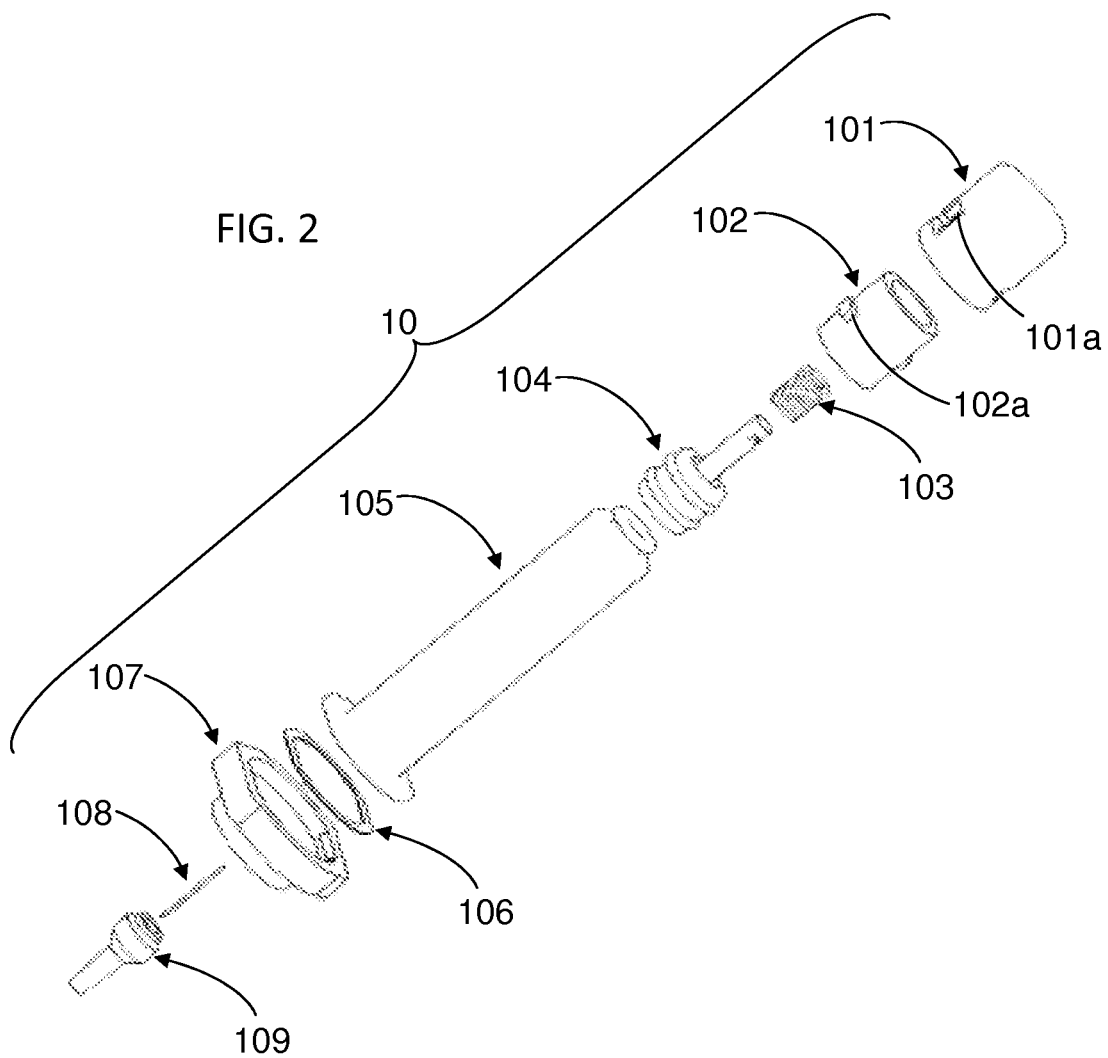
FIG. 2 is an exploded view of the exemplary injection device assembly according to the invention.
Figure 4:
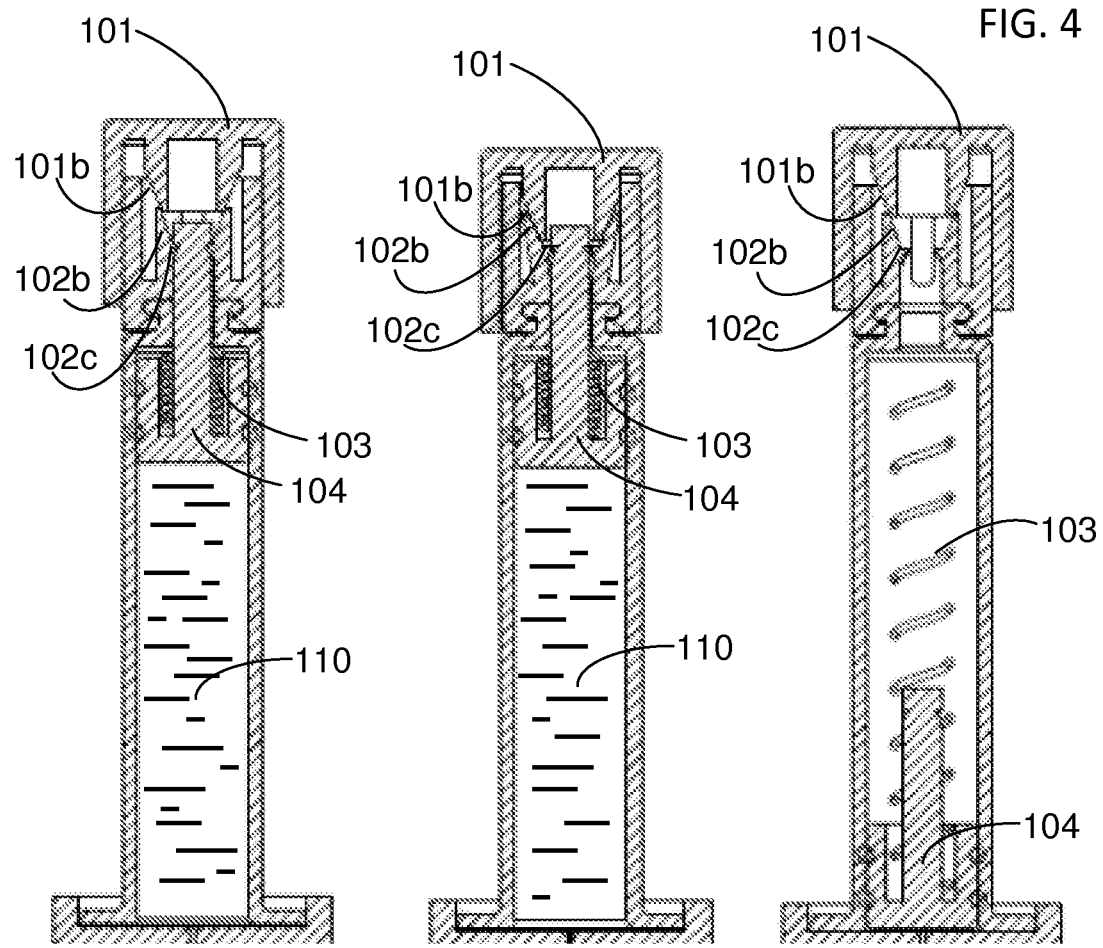
FIG. 4 shows a series of cross-sectional views of the activation and medication injection procedure of the exemplary injection device assembly according to the invention.

The present invention will become more fully understood from the detailed description given hereinbelow and the accompanying drawings which are given by way of illustration only, and thus, are not limitive of the present invention, and wherein:

The apparatus and methods presented herein can be used for injecting any of a variety suitable therapeutic agents or substances, such as a drug, into a patient. Initially it may be convenient to define that, the term "distal end" is meant to refer to the end of the injection device assembly inserted into the patient, Whereas the term "proximal end" is meant to refer to the end opposite to the "distal end" along the longitudinal axis of the device body. The words "upper", "lower", "right" and "left" designate directions in the drawings to which reference is made. The Words "inward" and "outward" refer to directions toward and away from, respectively, FIGS. 1-4 illustrate the construction and function mechanism of an exemplary injection device assembly 10 according to the invention. In this exemplary injection device assembly 10, a container body 105 can be made of either glass or plastic materials. A piston 104 is placed at a fixed position at the proximal end of the container body and restrained by a latch lock mechanism before use. The latch lock mechanism is formed between the piston 104 and connector 102. Push cap 101 is used to activate an automatic injection. The push cap 101 is engaged with a connector 102, through a guide key 102a provided on the connector 102 and a track 101a being defined on the push cap 101. This engagement prevents incidental activation of the device before use. During use, the push cap 101 is rotated to an activation position so that be push cap 101 can be pushed toward to the distal end of the device. With reference to FIGS. 3 and 3A, the injection device assembly 10 is shown with the piston 104 in a locked state. The piston 104 is restrained in the locked state, against biasing force of a spring 103, by deflectable latches formed between features 102c on the connector 102 and features 104a on the piston 104. The interengagement of features 102c and features 104a restricts distal movement of the piston 104 under force of the spring 103. The connector 102 is assembled with the container body 105 through a snap fit. The container body 105 is assembled with a needle cap 107 through another snap fit. With reference to FIG. 3B, an elastomeric seal ring 106 is used to keep the sterile seal between the container body 105 and the needle cap 107. In the case that the container body 105 is assembly with the needle cap 107 through bonding, for example, gluing or ultrasound welding, there is no need to use the elastomeric seal ring 106. Needle 108 is staked in the needle cap 107 through gluing or insert molding. A needle shield 109 is used to seal the needle 108. FIG. 4 depicts the activation and medication injection procedure of the injection device assembly 10 during use. Upon activation, the push cap 101 is pushed toward to the distal end of the device, a distally-directed tapered actuation surface 101b on the push cap 101 engages with the outwardly tapered engagement surfaces 102b on the connector 102 and push features 102c on the connector 102 outward. Through the contact of engagement surfaces, a predetermined downward movement of the push cap 101 causes the outward movement of the features 102c on the connector 102. The latch lock mechanism formed between the connector 102 and the piston 104 is released and the spring 103 drives the piston 104 to move toward the distal end of the device. Consequently, liquid medication 110 in the container body 105 is injected from the device into patient's body. Compared to traditional prefilled syringe based auto-injector device, this injection device assembly 10 has the piston locked at the fixed position and has much smaller overall size for the same injection volume.

Figure 5:
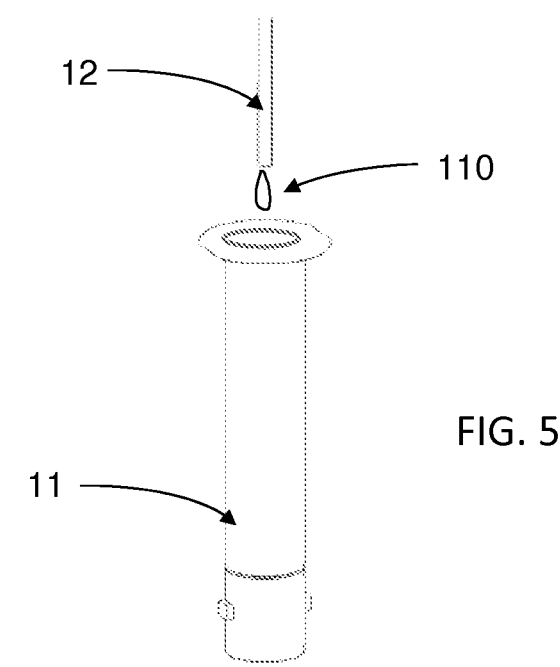
FIG. 5 shows the medication filling process to the container body sub-assembly of the exemplary injection device assembly according to the invention.

FIG. 5 illustrates a medication filling process for the injection device assembly 10. Here, the filling process happens at the distal end of the container body 105. The liquid medication 110 is filled through a filling needle 12 into a container body sub-assembly 11. The container body sub-assembly 11 is formed by the connector 102, the spring 103, the piston 104 and the container body 105. After filling, a needle assembly, which is formed by the sealing ring 106, the needle cap 107, needle 108 and the needle shield 109, is assembled with the container body sub-assembly 11. Therefore, air bubble size can be greatly reduced and even eliminated.

FIGS. 6, 6A and 6B show a packaging configuration of the container body sub-assembly 11. This packaging configuration of the container body sub-assembly 11 is compatible with the standard prefilled syringe packaging, i.e., nest-tub package, existed in prior art. This demonstrates that the device can be filled and assembled using existing assembly and packaging processes for pre-filled syringe. In FIG. 6, a nest 13 for the container body sub-assembly 11 is provided being a panel with a plurality of spaced-apart openings 131 and container body holding features 131a and 131b for holding the container body sub-assembly 11 in place. In the embodiment illustrated, openings 131 and holding features 131a/131b are arranged in a series of rows and columns and are uniformly spaced apart. The holding features 131a and 131b are further optimized, compared with the standard prefilled syring packaging nest. In FIGS. 6A and 6B, for each opening 131 in the nest 13, features 131a support the container body sub-assembly 11, and features 131b prevent the container body sub-assembly from rotating and moving up/down in the opening 131. This nest design can also be used for packaging the standard pre-filled syringe existed in prior art.

Exemplary methods for filling and packaging syringes and other medical containers are disclosed in U.S. Pat. Nos. 6,189,292; 7,428,807; 7,431,157 and 8,196,741, et al., which are hereby incorporated by reference in their entirety.

In this invention, the other injection device assembly embodiments can utilize a similar filling and packaging processes illustrated in FIGS. 6, 6A and 6B.

Figure 7:
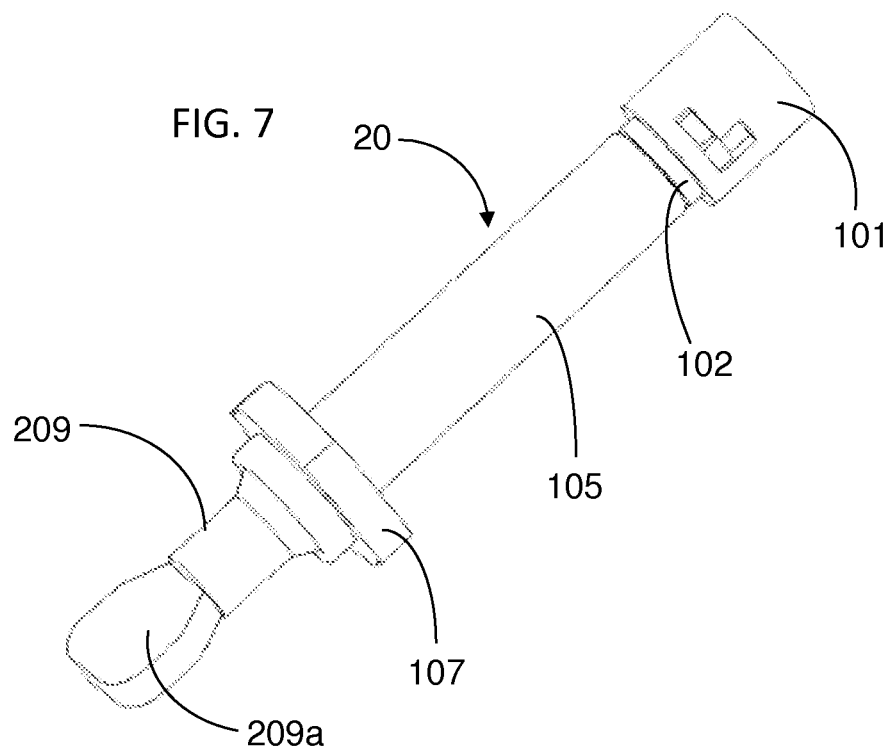
FIG. 7 is a perspective view of the first alternative injection device assembly according to the invention.
Figure 8:
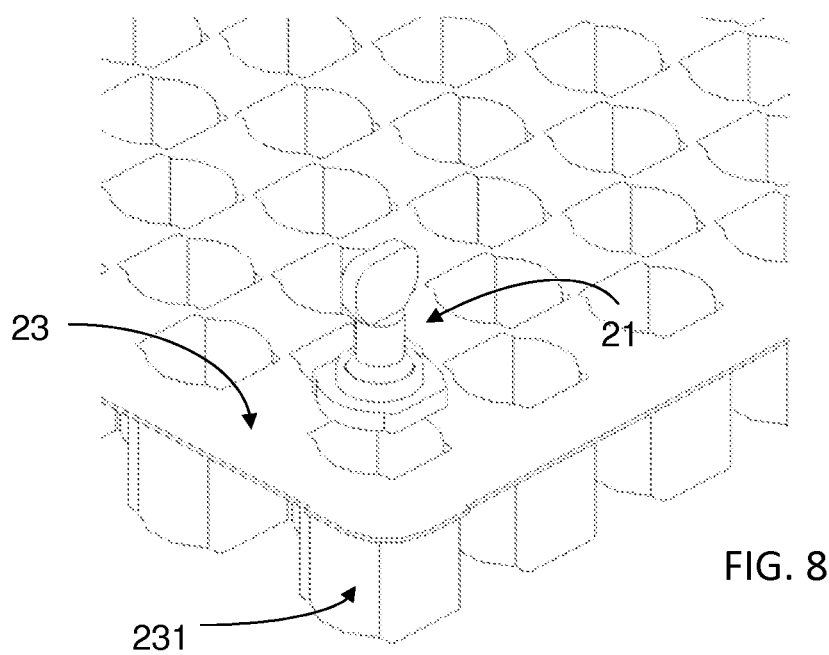
FIG. 8 is the packaging configuration for a needle assembly of the first alternative injection device assembly according to the invention.

FIG. 7 shows the first alternative injection device assembly 20. In this embodiment, a user-friendly needle sub-assembly 21 is introduced. The user-friendly needle sub-assembly is formed by the seal ring 106, the needle cap 107, the needle 108 (hidden in FIG. 7) and an improved needle shield 209. The improved needle shield 209 has a finger gripping feature 209a so that the needle shield can be easily removed by users. FIG. 8 shows a packaging nest 23 for the needle sub-assemly 21. The needle sub-assemblies 21 can be packaged into pockets 231 of the packaging nest 23. The needle sub-assembly packaging nest 23 is similar to the nest packaging configuration for rubber piston for pre-filled syringe existed in prior art.

Figure 9:
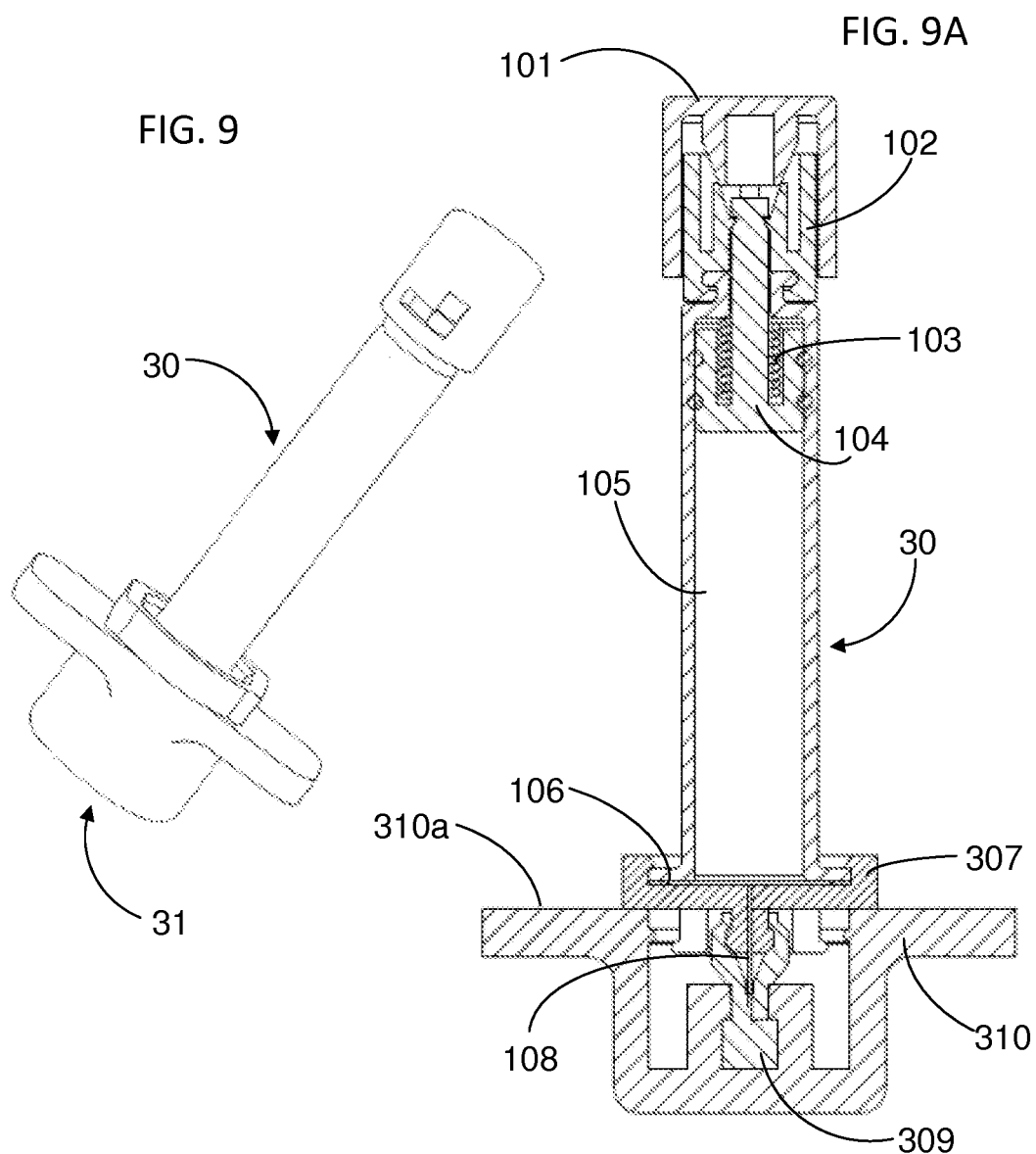
FIG. 9 is a perspective view of the second alternative injection device assembly according to the invention.

FIGS. 9 and 9A show the second alternative injection device assembly 30. In this embodiment, a user-friendly needle sub-assembly 31 is introduced. The user-friendly needle sub-assembly 31 is formed by the seal ring 106, a needle cap 307, the needle 108, an improved needle shield 309 and a needle puller 310. The needle shield puller 310 has a wider wing features 310a so that the needle shield can be easily removed by users.

Figure 10:
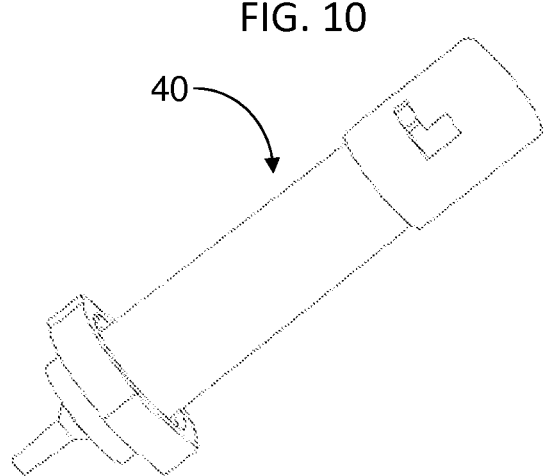
FIG. 10 is a perspective view of the third alternative injection device assembly according to the invention.
Figure 10A:
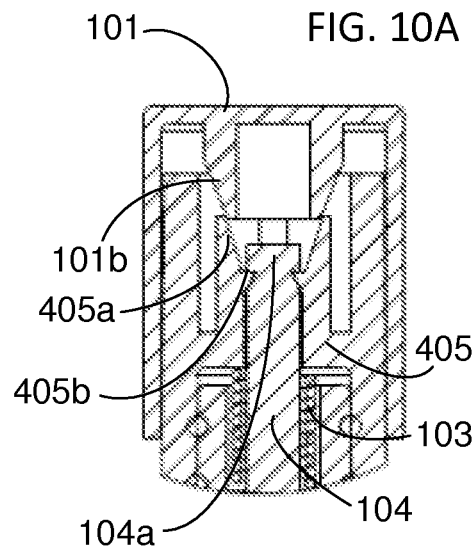
FIG. 10A is a cross-sectional detailed view of the third alternative injection device assembly according to the invention.
Figure 11:
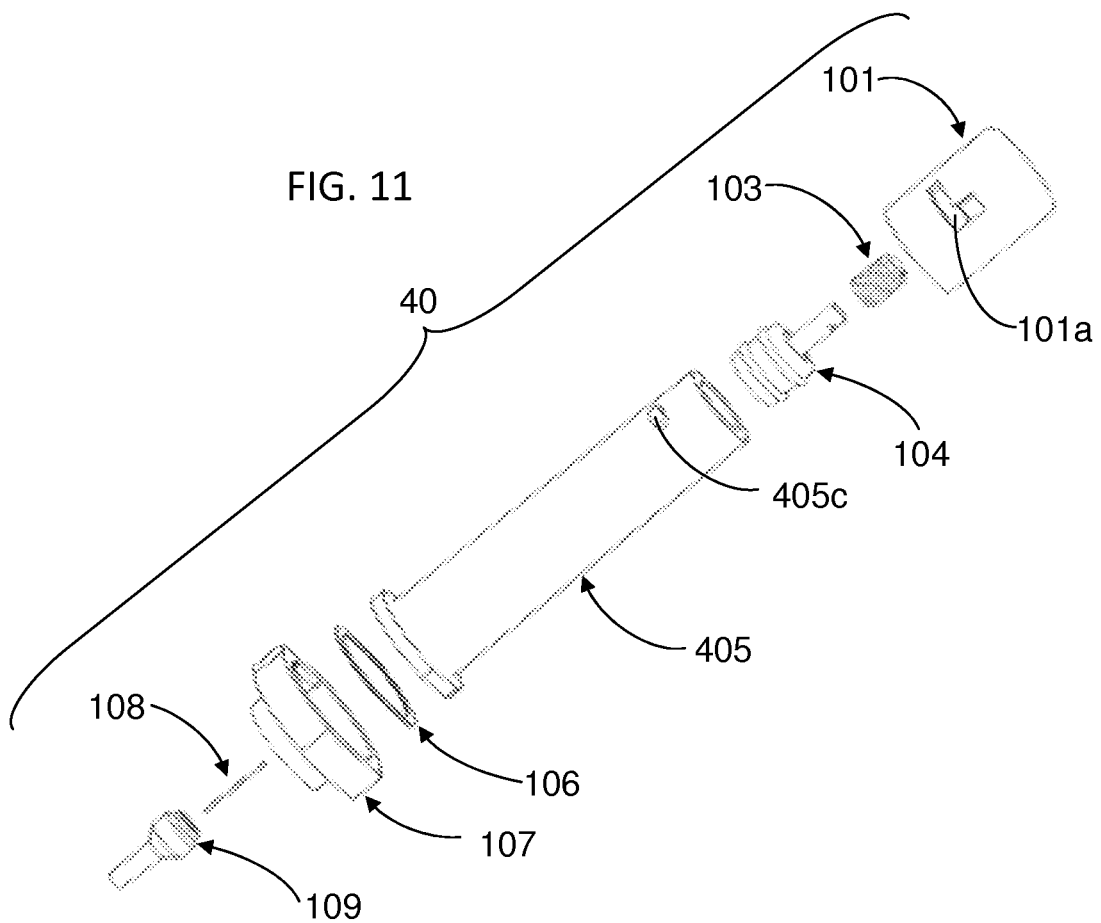
FIG. 11 is an exploded view of the third alternative injection device assembly according to the invention.
Figure 16:
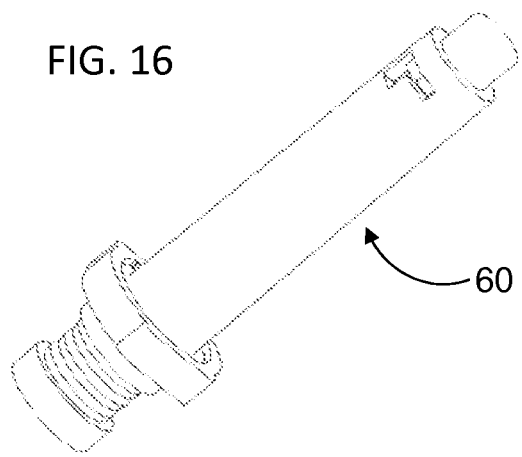
FIG. 16 is a perspective view of the fifth alternative injection device assembly according to the invention.
Figure 17:
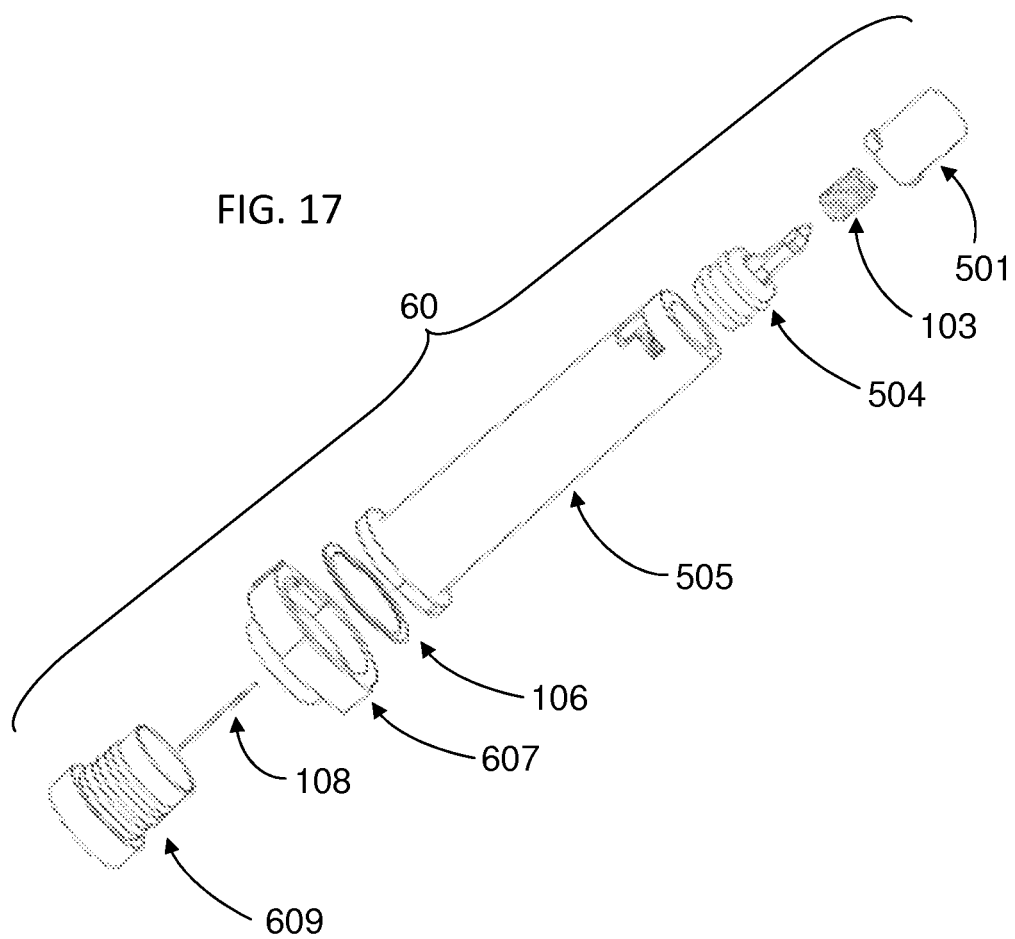
FIG. 17 is an exploded view of the fifth alternative injection device assembly according to the invention.
Figure 19:
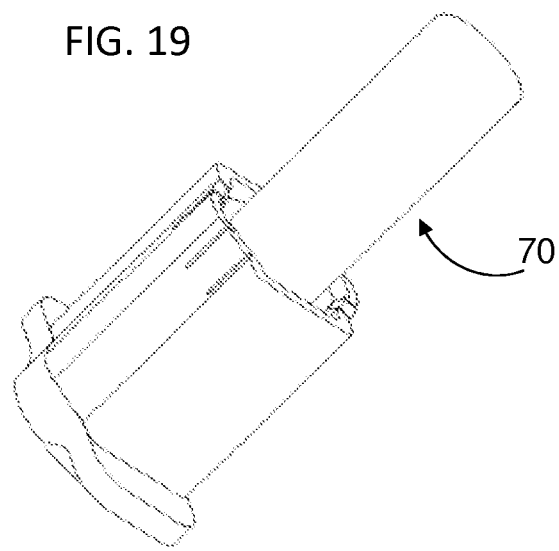
FIG. 19 is a perspective view of the sixth alternative injection device assembly according to the invention.
Figure 20:
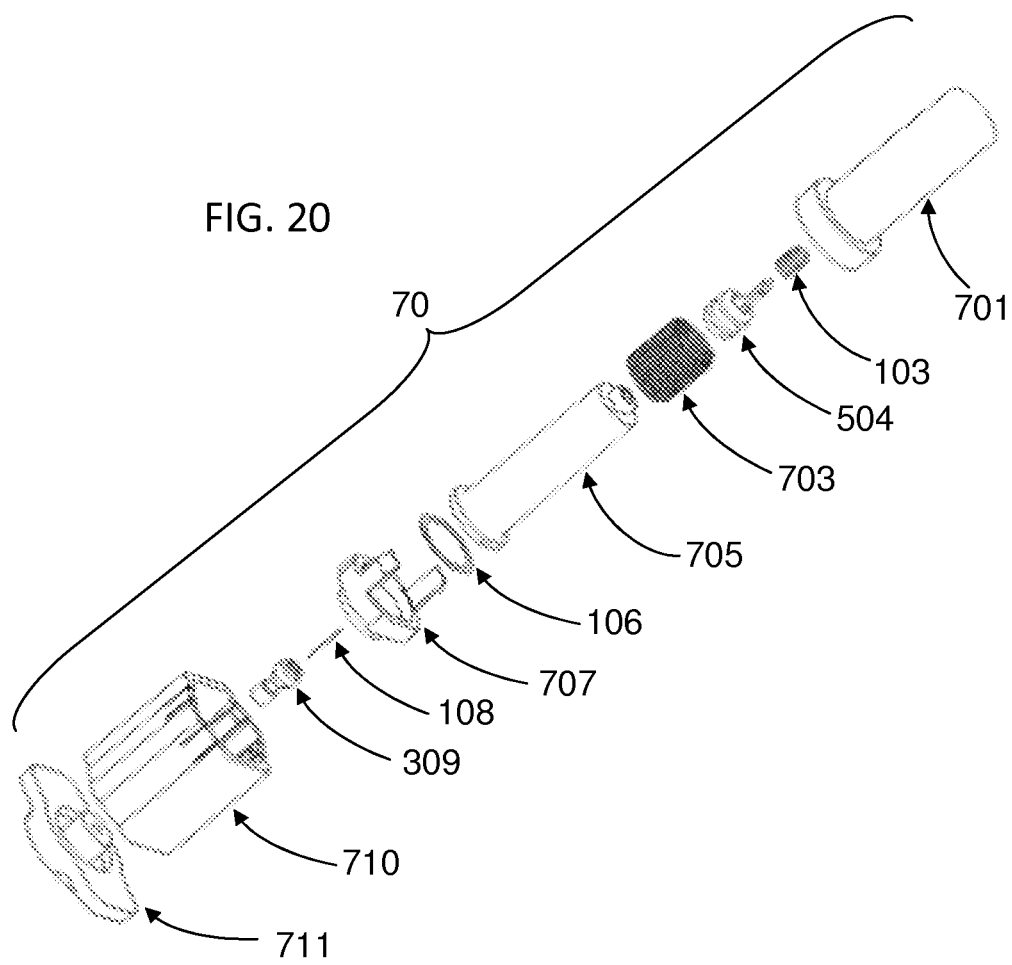
FIG. 20 is an exploded view of the sixth alternative injection device assembly according to the invention.
Figure 23:
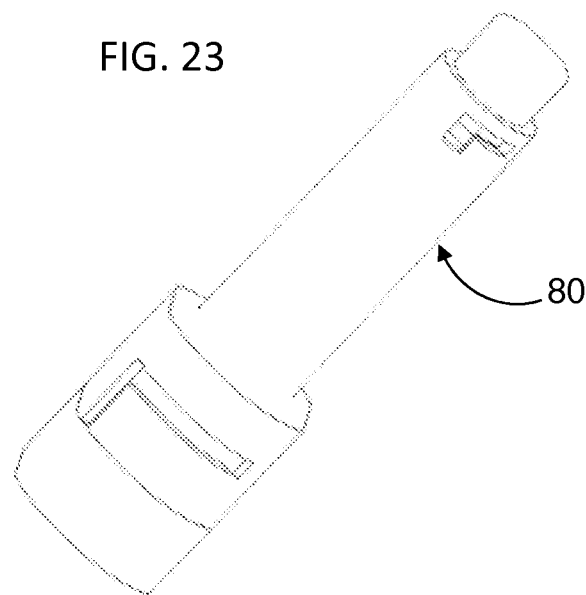
FIG. 23 is a perspective view of the seventh alternative injection device assembly according to the invention.
Figure 24:
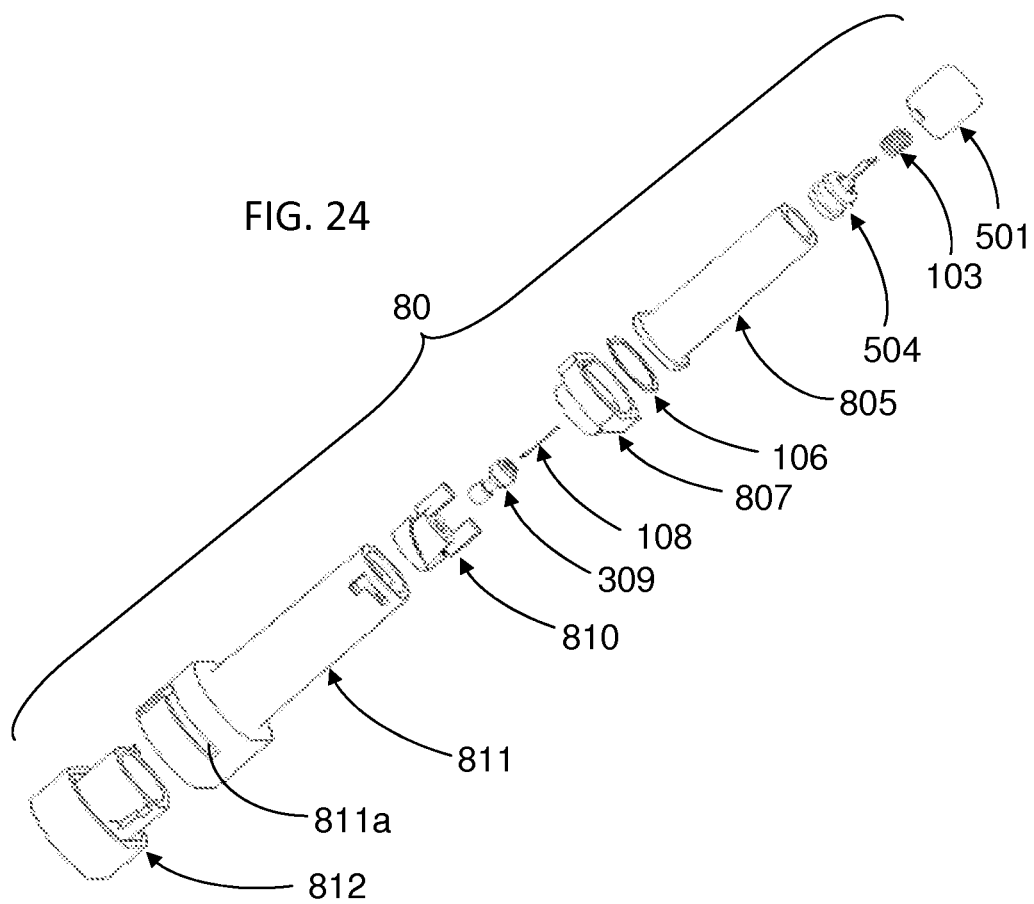
FIG. 24 is an exploded view of the seventh alternative injection device assembly according to the invention.

FIGS. 10, 10A and 11 show the third alternative injection device assembly 40. In this embodiment, a container body 405 is made of plastic materials. Because design features can be injection molded on plastic parts, the features on the connector 102 in injection device assembly 10 are integrated into the container body 405 here. FIG. 10A is a detailed view of the proximal end of the injection device assembly 40. The proximal end of the container body 405 has features 405a and 405b for the releasable latch mechanism for controlling the automatic injection. Features 405c on the container body 405 are designed to form guide key/track engagement with push cap 101.

FIGS. 12, 12A and 13 show the fourth alternative injection device assembly 50. In this embodiment, a container body 505 is made of plastic materials. A push cap 501 has the smaller external diameter than the external tubular diameter of the container body 505. Consequently, this embodiment is more compatible with the nest packaging configuration depicted in FIGS. 6, 6A and 6B. The push cap 501 is engaged with the container body 505, through a guide key 501a provided on the push cap 501 and a track 505c being defined on the container body 505. FIG. 12A is a detailed view of the proximal end of the injection device assembly 50. Upon activation, the push cap 501 is pushed toward the distal end of the device, a distally-directed chamfered actuation surface 501b on the push cap 501 engages with a chamfered engagement surface 504a on the piston 504 and push a restraining feature 504b on the piston 504 bend toward left and away from a feature 505a on the container body 505. Then, the latch lock mechanism formed between the the piston 504 and the container body 505 is released and the spring 103 drives the piston 504 to move toward the distal end of the device.

FIGS. 14 and 14A show the piston 504. Here, the piston 504 is formed by a rigid core 504c and one or more elastomeric seal rings 504d. FIGS. 15 and 15A show a piston 5041, as an alternative to the piston 504. The piston 5041 is formed by a rigid core 5041a and an elastomeric component 5041b wrap around the rigid core 5041a. The elastomeric component 5041b can be standard syringe rubber plunger. The materials construction for the piston 504 herein is applicable to the piston 104.

FIGS. 16-18B show the fifth alternative injection device assembly 60. In this embodiment, the same push cap 501, piston 504 and container body 505 are used, as to the components in the injection device assembly 50. In FIG. 18, a cross-sectional view, preferably, the proximal end of the container body 505e has a slightly smaller inner diameter than the inner diameter at the distal end of the container body 505f. This design feature provides following two advantages—1) When the piston 504 moves toward the the distal end of the container body 505f, the friction force between the piston 504 and the container body 505 will be less because of the less amount of interference between the piston 504 and the container body 505. Therefore, the unnecessary high spring force required for the spring 103 can be avoided. 2) The tapered construction of container body inner cylinder can make the injection molding process much easier because the part can be easily removed from the molding tool during injection molding manufacturing process. FIGS. 18A and 18B are detailed views of the needle assembly for the fifth alternative injection device assembly 60. The needle assembly is formed by the seal ring 106, a needle cap 607, the needle 108, a compressible needle shield sub-assembly 609. The compressible needle shield sub-assembly 609 is formed by a compressible component 609a, a rigid needle shield frame 609b and an elastomeric needle shield 609c. During injection, the injection device assembly 60 is pushed against patient's skin at the injection site. The compressible component 609a collapses. The needle 108 pierces the elastomeric needle shield 609c and is inserted into skin for injection. This design allows user to skip the mannual needle shield removal step before injection.

FIGS. 19-22 show the sixth alternative injection device assembly 70. With reference to FIGS. 21 and 22, before injection, the needle shield 309 is removed by pulling away a needle shield puller 711. Upon activation, a push sleeve 701 is pushed toward to the distal end of the injection device assembly 70, a distally-directed chamfered actuation surface 701a on the push sleeve 701 engages with the chamfered engagement surface 504a on the piston 504 and push the restraining feature 504b on the piston 504 bend toward left and away from the feature 705a on the container body 705. The latch lock mechanism formed between the the piston 504 and the container body 705 is released and the spring 103 drives the piston 504 to move toward to the distal end of the device. The container body 705 is shown together with a needle cap 707 in a restrained state before injection. Needle 108 is staked in the needle cap 707 through gluing or insert molding. Needle shield 309 is used to seal the needle 108. The needle cap 707 is restrained, against biasing force of an driving spring 703, by the deflectable latches formed between features 707a on the needle cap 707 and features 710b on the housing 710. When the push sleeve 701 is pushed toward the distal end of the device, a distally-directed tapered actuation surface 701b on the push sleeve 701 engages with a inwardly tapered engagement surfaces on features 707a on the needle cap 707. Through contacts of the engagement surfaces, a predetermined downward movement of the push sleeve 701 causes the inward movement of the features 707a on the needle cap 707. The latch lock mechanism formed between the needle cap 707 and the housing 710 is released and a driving spring 703 drives the needle cap 707 together with the container body 705 and the needle 108 to move toward the distal end of the device. Consequently, the needle 108 is inserted into patient's body for injection. Features 710a on the housing 710 is to stop the further distal movement of the needle cap 707. In this embodiment, the push sleeve 701 triggers the release of both the piston 504 and the needle cap 707 when the push sleeve 701 is pushed toward the distal end of the injection device assembly 70.

Figure 27:
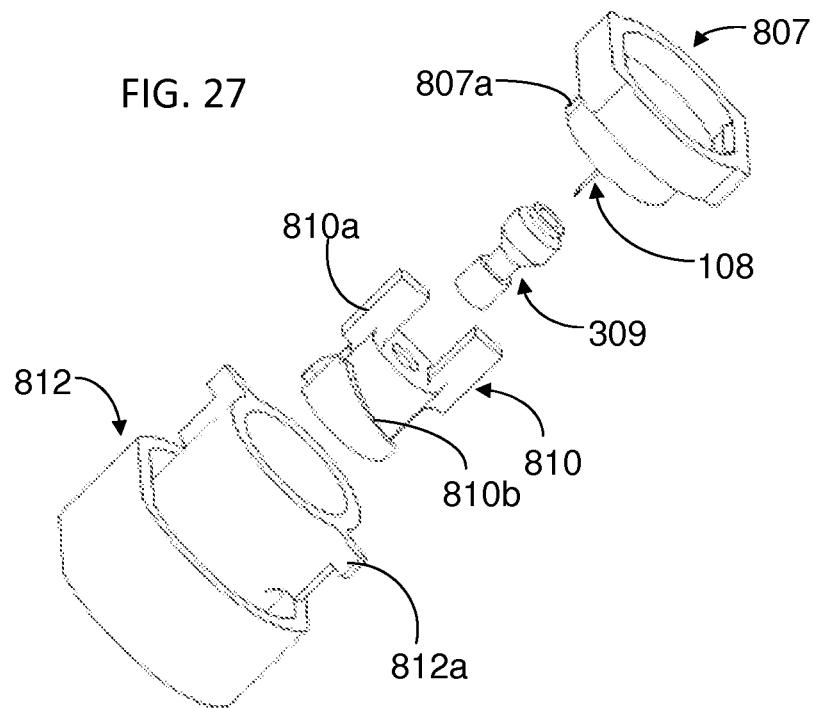
FIG. 27 is an exploded view of the needle sub-assembly of the seventh alternative injection device assembly according to the invention.
Figure 28:
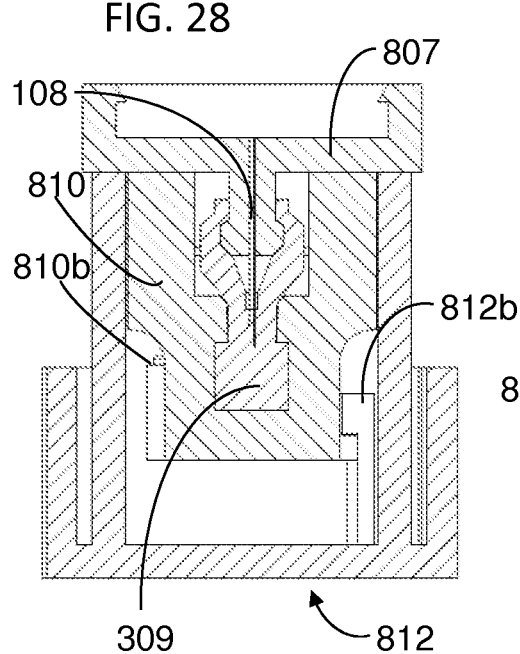
FIG. 28 and FIG. 29 are cross-sectional views of the needle sub-assembly of the seventh alternative injection device assembly according to the invention.
Figure 29:
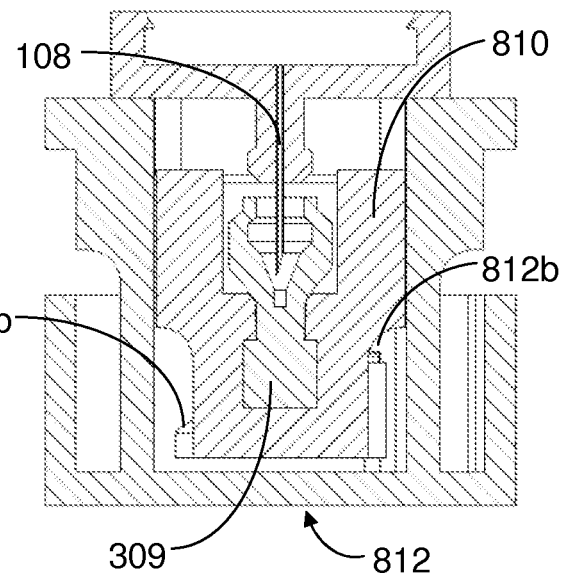
Figure 34:
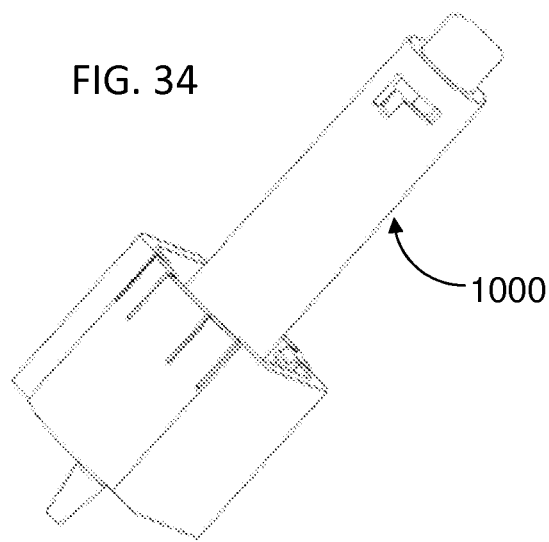
FIG. 34 is a perspective view of the ninth alternative injection device assembly according to the invention.
Figure 35:
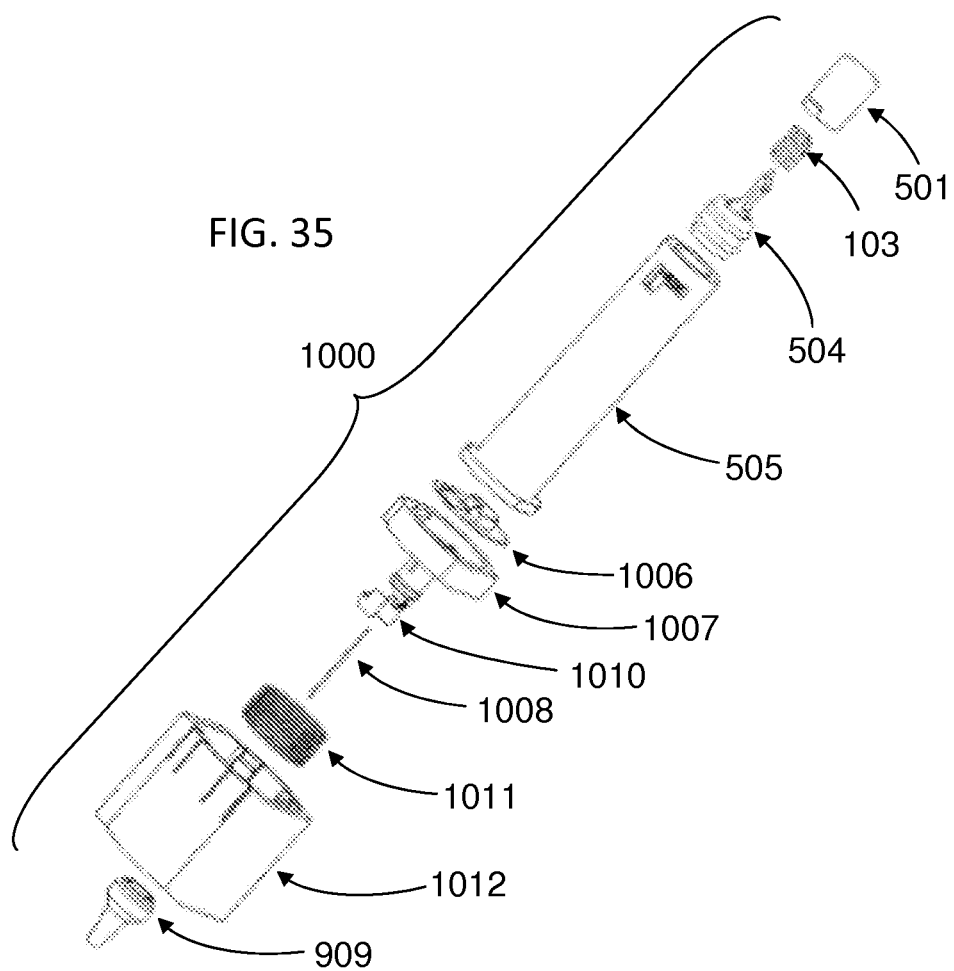
FIG. 35 is an exploded view of the ninth alternative injection device assembly according to the invention.
Figure 36:
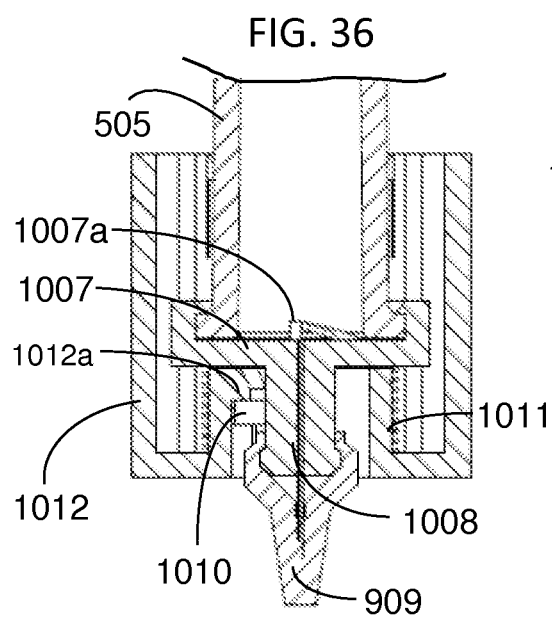
FIG. 36, FIG. 36A, FIG. 37, FIG. 37A, FIG. 38 and FIG. 38A show the mechanism of the needle sub-assembly of the ninth alternative injection device assembly according to the invention.
Figure 36A:
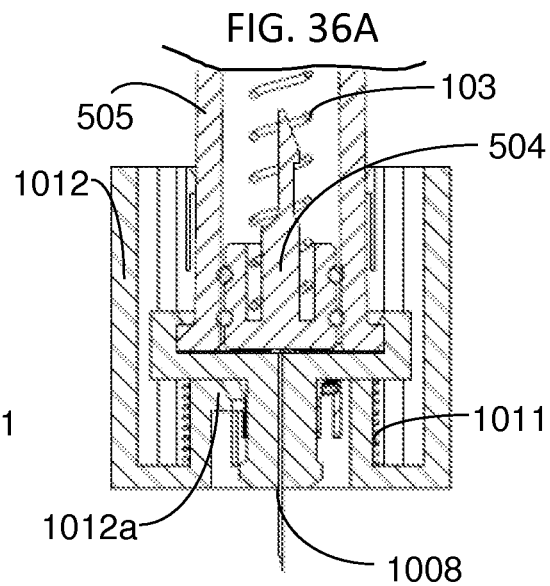
Figure 37:
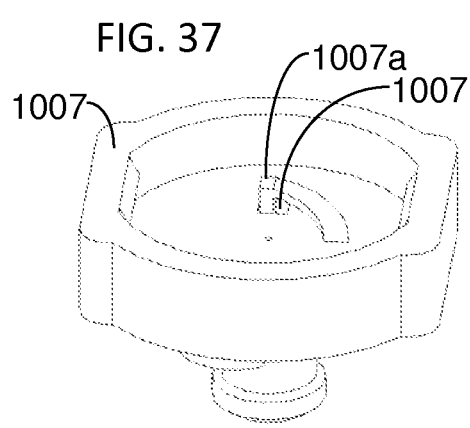
Figure 37A:
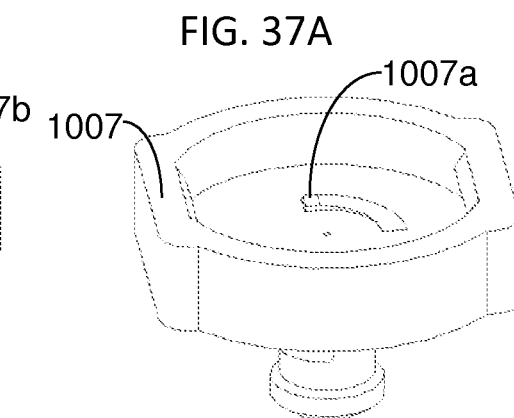
Figure 38:
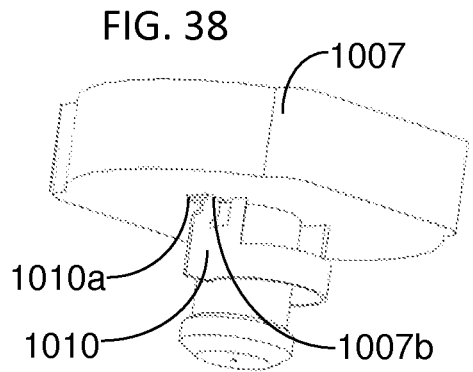
Figure 38A:
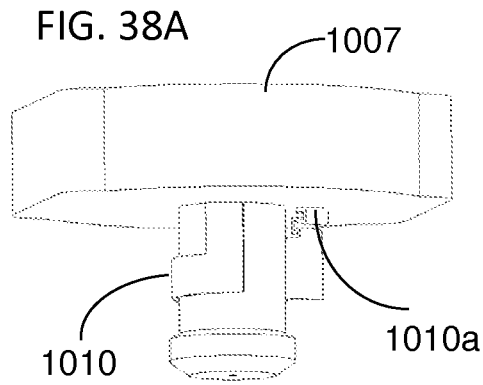

FIGS. 23-29 show the seventh alternative injection device assembly 80. With reference to FIG. 25, a container body 805, together with a needle cap 807, the seal ring 106 and the needle 108, is restrained between a housing 811 and a bottom cap 812 before use. The piston 504 is locked by a releasable latch mechanism formed between the feature 504b on the piston 504 and a feature 811a on the housing 811. Theses design features ensure that the pison 504 is locked at a fixed position at the proximal end of the container body 805 before use. During use of the injection device assembly 80, user first remove the needle shield 309 through s combined action of a needle shield puller 810 and a bottom cap 812. Upon activation, the push cap 501 is pushed toward the distal end of the injection device assembly 80. The predetermined movement of the push cap 501 release the latch mechanism formed between the piston 504 and the housing 811. Shown as in FIG. 26, the spring 103 is released and drives the piston 504 move toward the distal end of the injection device assembly 80. Because of the hydraulic resistance from the liquid medication, the container body 805, together with the needle cap 807, the seal ring 106 and the needle 108, also moves toward to the distal end of the injection device assembly 80. In this embodiment, the release of the spring 103 serves two functions. One of the two functions is to push the container body 805 and the needle cap 807 and the needle 108 move in order to insert needle into patient body. The other function is to drive the piston move to push the medication into patient body. With reference to FIGS. 27-29, another design feature for the injection device assembly 80 is that a cam mechanism design is introduced for the needle shield 309 removal procedure. The cam mechanism is formed between the cam surfaces 810b on the needle shield puller 810 and a finger feature 812b on the bottom cap 812. During the needle shield 309 removal, user first twists the bottom cap 812. The bottom cap rotates following a guide key feature 812a. The guide key feature 812a moves along track features 811a on the housing 811. Because the rotational movement of the needle shield puller 810 is restricted by the engagement between features 810a on the needle shield puller 810 and features 807a on the needle cap 807, the rotation of the bottom cap causes the longitudinal movement of the needle shield puller 810 through the cam mechanism. The longitudinal movement of the needle shield puller 810, toward the distal end of the injection device assembly 80, causes the separation of the needle shield 309 from the needle 108. This design feature avoids the pulling force applied to the needle 108, the needle cap 807, the seal ring 106 and the container body 805, during the needle shield 309 removal along the longitudinal direction of the injection device assembly 80. After the needle shield 309 is completely separated from the needle 108, the bottom cap 812, together with the needle shield puller 810 and the needle shield 309, is removed, along the track features 811 a on the housing 811, to be ready for injection.

FIGS. 30-33 show the eighth alternative injection device assembly 90. In this embodiment, a needle retraction design is introduced as an example of needle protection at the end of medication injection. Before injection, a needle shield 909 is removed from a needle cap 907. With reference to FIGS. 32 and 33, at the end of the medication injection, a piston 904 moves to the distal end of the container body 505, driven by the spring 103. A distally-directed tapered actuation feature 904a on the piston 904 pushes locking fingers 907a on the needle cap 907 outward. Consequently, a needle retraction spring 910 is released and the needle retraction spring 910 pushes a needle holder 911 and a needle 908 (bonded together) move into a retaining cavity 904b provided on the piston 904. Consequently, the needle is hidden after the injection procedure. An elastomeric feature 911a on the needle holder 911 functions as sterility seal for the system.

FIGS. 34-38A show the tenth alternative injection device assembly 1000. With reference to FIGS. 36-38A, at the end of the medication injection, the piston 504 moves to the distal end of the container body 505 and pushes a triggering fiinger feature 1007a on needle cap 1007 lower toward the distal end of the injection device assembly 1000 through a pre-formed opening 1007b on the needle cap 1007. The triggering finger feature 1007a then releases a moving end 1010a of a resilient metal ring 1010. The resilient metal ring 1010 moves axially inward to the axial center of the needle cap 1007 and release the lock mechanism formed between the resilient metal ring 1010 and a locking finger 1012a on a protection sheath 1012. After the lock mechanism is released, a sheath driving spring 1011 drives the protection sheath 1012 move toward the distal end of the injection device assembly 1000. The protection sheath 1012 extend outward to cover a needle 1008 and reduce needle injury after medication injection. In this embodiment, a seal ring 1006 is used to seal the gap between the needle cap 1007 and the container body 505, as well as the pre-formed opening 1007b.

FIGS. 39-42 show an injection device assembly 1100 as an alternative to the injection device assembly 1000. With reference to FIGS. 41 and 42, instead of using the resilient metal ring 1010, a combination of an alternative resilient metal ring 1110 and a plastic block ring 1113 is used in this embodiment to control the movement of the protection sheath 1012. The lock mechanism is formed between the plastic blocking ring 1113 and the locking finger 1012a on the protection sheath 1012. At the end of the medication injection, the piston 504 moves to the distal end of the container body 505 and pushes a triggering fiinger feature 1107a on needle cap 1107 lower toward the distal end of the injection device assembly 1100. The triggering finger feature 1107a then releases a moving end 1110a of the resilient metal ring 1110. The resilient metal ring 1110 moves inward to the axial center of the needle cap 1107 and rotate the plastic blocking ring 1113. When the plastic blocking ring 1113 rotates, an opening portion 1113b on the plastic blocking ring 1113 moves to the location originally occupied by a blocking portion 1113a on the plastic blocking ring 1113. The opening portion 1113b on the plastic blocking ring 1113 allows the locking finger 1012a on the protect sheath 1012 free to move. Consequently, the protect sheath 1012 moves toward the distal end of the injection device assembly 1100, driven by the sheath driving spring 1011.

For injection device assemblies 90, 1000 and 1100, the end-of-injection events, including needle retraction and needle protection sheath extending out, are triggered directly by the piston 504 arriving at the distal end of the container body 505. By this way, the end-of-injection events can be prevented from happening pre-maturally.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An automatic injection device comprising:
 a container body having an interior surface, an exterior surface, a distal end, and a proximal end, wherein said distal end of said container body has an outward projection;
 a piston having an elastomeric component, said elastomeric component of said piston is disposed between said distal end and said proximal end of said container body, wherein said elastomeric component abuts said proximal end of said container body and said piston is configured to slide along said interior surface of said container body;
 a resilient member enclosed between said proximal end of said container body and said elastomeric component of said piston, biasing against said proximal end of said container body;
 a restraining means configured to restrain said piston from moving distally under biasing of said resilient member;
 a cap attached at said distal end of said container body through said outward projection at said distal end of said container body; and
 a reservoir defined by said container body and said cap, wherein said reservoir is filled with medication.

2. The automatic injection device as in claim 1 further comprising a needle attached to said cap.

3. The automatic injection device as in claim 2 further comprising a needle.

4. The automatic injection device as in claim 3 wherein said needle shield being pierced by said needle during medication injection.

5. The automatic injection device as in claim 2 further comprising an automatic needle insertion means configured to automatically insert said needle into medication injection site.

6. The automatic injection device as in claim 2 further comprising a needle retraction means configured to retract said needle.

7. The automatic injection device as in claim 2 further comprising an automatic needle protection means configured to extend a sheath out to at least partially cover said needle.

8. The automatic injection device as in claim 1, wherein said container body has a tubular shape, wherein inner diameter at said proximal end of said container body is smaller than inner diameter at said distal end of said container body.

9. The automatic injection device as in claim 1 further comprising a seal member placed between said container body and said cap.

10. A packaging assembly for an automatic injection device, comprising:
 a container body assembly comprising a container body having an interior surface, an exterior surface, a distal end, and a proximal end, wherein said distal end of said container body has an outward projection; a piston having an elastomeric component, said elastomeric component of said piston is disposed between said distal end and said proximal end of said container body, wherein said elastomeric component abuts said proximal end of said container body and said piston is configured to slide along said interior surface of said container body; a resilient member enclosed between said proximal end of said container body and said elastomeric component distal end of said piston, biasing against said proximal end of said container body; a reservoir defined by said container body and a cap, wherein said reservoir is configured to be filled with a medicament and a restraining means configured to restrain said piston from moving distally under biasing of said resilient member;
 the cap configured to attach at said distal end of said container body through said outward projection at said distal end of said container body;
 a panel; and
 a plurality of openings defined in said panel, wherein said panel and said plurality of openings are integrally formed as a unitary structure and each of said openings configured to removeably receive each of said container body assembly.

11. The packaging assembly as in claim 10 wherein said opening removeably receives said container body assembly while said distal end of said container body is facing up.

12. The packaging assembly as in claim 10 wherein said outward projection at said distal end of said container body lands on said opening in said panel.

13. The packaging assembly as in claim 10 wherein said opening defines a holding means configured to stabilize said container body assembly.

14. The packaging assembly as in claim 10 further comprising a nest having a plurality of holders, wherein each of said holders is configured to removeably receive said cap.

15. A method of producing an automatic injection device comprising the steps of:
- providing a container body assembly comprising a container body having an interior surface, an exterior surface, a distal end, and a proximal end, wherein said distal end of said container body has an outward projection; a piston having an elastomeric component, said elastomeric component of said piston is disposed between said distal end and said proximal end of said container body, wherein said elastomeric component abuts said proximal end of said container body and said piston is configured to slide along said interior surface of said container body; a resilient member enclosed between said proximal end of said container body and said elastomeric component of said piston, biasing against said proximal end of said container body; and a restraining means configured to restrain said piston from moving distally under biasing of said resilient member;
- placing said container body assembly while said distal end of said container body is facing up;
- filling medication from said distal end of said container body; and
- attaching a cap at said distal end of said container body through said outward projection at said distal end of said container body.

\* \* \* \* \*